(12) United States Patent
Rigo et al.

(10) Patent No.: US 9,518,259 B2
(45) Date of Patent: Dec. 13, 2016

(54) COMPOUNDS AND METHODS FOR MODULATING INTERACTION BETWEEN PROTEINS AND TARGET NUCLEIC ACIDS

(75) Inventors: Frank Rigo, Carlsbad, CA (US); C. Frank Bennett, Carlsbad, CA (US); Adrian R. Krainer, Huntington Station, NY (US); Yimin Hua, Jericho, NY (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 13/703,322

(22) PCT Filed: Jun. 15, 2011

(86) PCT No.: PCT/US2011/040581
§ 371 (c)(1),
(2), (4) Date: Jul. 19, 2013

(87) PCT Pub. No.: WO2011/159836
PCT Pub. Date: Dec. 22, 2011

(65) Prior Publication Data
US 2013/0289092 A1   Oct. 31, 2013

Related U.S. Application Data

(60) Provisional application No. 61/355,125, filed on Jun. 15, 2010.

(51) Int. Cl.
| | |
|---|---|
| *C12N 15/11* | (2006.01) |
| *A61K 48/00* | (2006.01) |
| *C12Q 1/68* | (2006.01) |
| *C12N 15/113* | (2010.01) |
| *C07H 21/04* | (2006.01) |

(52) U.S. Cl.
CPC ........... *C12N 15/113* (2013.01); *C12N 15/111* (2013.01); *C12N 2310/11* (2013.01); *C12N 2310/321* (2013.01); *C12N 2310/322* (2013.01); *C12N 2310/3231* (2013.01); *C12N 2310/3341* (2013.01); *C12N 2310/341* (2013.01); *C12N 2310/3525* (2013.01); *C12N 2310/3533* (2013.01); *C12N 2320/33* (2013.01)

(58) Field of Classification Search
None
See application file for complete search history.

(56) References Cited

U.S. PATENT DOCUMENTS

| | | | |
|---|---|---|---|
| 3,687,808 A | 8/1972 | Merigan et al. | |
| 4,845,205 A | 7/1989 | Huynh Dinh et al. | |
| 5,130,302 A | 7/1992 | Spielvogel et al. | |
| 5,134,066 A | 7/1992 | Rogers et al. | |
| 5,175,273 A | 12/1992 | Bischofberger et al. | |
| 5,367,066 A | 11/1994 | Urdea et al. | |
| 5,432,272 A | 7/1995 | Benner | |
| 5,457,187 A | 10/1995 | Gmelner et al. | |
| 5,459,255 A | 10/1995 | Cook et al. | |
| 5,484,908 A | 1/1996 | Froehler et al. | |
| 5,502,177 A | 3/1996 | Matteucci et al. | |
| 5,525,711 A | 6/1996 | Hawkins et al. | |
| 5,552,540 A | 9/1996 | Haralambidis | |
| 5,587,469 A | 12/1996 | Cook et al. | |
| 5,594,121 A | 1/1997 | Froehler et al. | |
| 5,596,091 A | 1/1997 | Switzer | |
| 5,614,617 A | 3/1997 | Cook et al. | |
| 5,645,985 A | 7/1997 | Froehler et al. | |
| 5,681,941 A | 10/1997 | Cook et al. | |
| 5,750,692 A | 5/1998 | Cook et al. | |
| 5,763,588 A | 6/1998 | Matteucci et al. | |
| 5,830,653 A | 11/1998 | Froehler et al. | |
| 6,005,096 A | 12/1999 | Matteucci et al. | |
| 6,210,892 B1 | 4/2001 | Bennett et al. | |
| 6,268,490 B1 | 7/2001 | Imanishi et al. | |
| 6,525,191 B1 | 2/2003 | Ramasamy | |
| 6,670,461 B1 | 12/2003 | Wengel et al. | |
| 6,770,748 B2 | 8/2004 | Imanishi et al. | |
| 6,794,499 B2 | 9/2004 | Wengel et al. | |
| 7,034,133 B2 | 4/2006 | Wengel et al. | |
| 7,053,207 B2 | 5/2006 | Wengel | |
| 7,399,845 B2 | 7/2008 | Seth et al. | |
| 7,427,672 B2 | 9/2008 | Imanishi et al. | |
| 8,129,515 B2 | 3/2012 | Esau et al. | |
| 8,637,478 B2 | 1/2014 | Bennett | |
| 2004/0171570 A1 | 9/2004 | Allerson et al. | |
| 2005/0130923 A1 | 6/2005 | Bhat et al. | |
| 2006/0172962 A1* | 8/2006 | Vickers et al. | 514/44 |

(Continued)

FOREIGN PATENT DOCUMENTS

| | | |
|---|---|---|
| WO | WO 99/14226 | 3/1999 |
| WO | WO 2004/106356 | 12/2004 |
| WO | WO 2007002390 A2 * | 1/2007 |
| WO | WO 2007/028065 | 3/2007 |
| WO | WO 2007028065 A2 * | 3/2007 |

(Continued)

OTHER PUBLICATIONS

Alló et al., Control of alternative splicing through siRNA-mediated transcriptional gene silencing, 2009, Nature Structural & Molecular Biology, vol. 16, pp. 717-724.*
Jirka et al., Evaluation of exon skipping activity of 2'-deoxy-2'-fluoro antisense oligonucleotides for Duchenne muscular dystrophy, Neuromuscular Disorders, 2014, vol. 24, pp. 827-828.*

(Continued)

*Primary Examiner* — Dana Shin
(74) *Attorney, Agent, or Firm* — Ionis Pharmaceuticals, Inc. Patent Dept.

(57) ABSTRACT

Provided herein are antisense compounds and methods for recruiting one or more non-cleaving protein to a target nucleic acid in a cell. In certain instances such recruitment of a non-cleaving protein alters the function or activity of the target nucleic acid. In certain such instances, the target nucleic acid a pre-mRNA and the recruitment of the non-cleaving protein results in a change in splicing of the pre-mRNA.

14 Claims, 4 Drawing Sheets

(56) References Cited

U.S. PATENT DOCUMENTS

| | | | |
|---|---|---|---|
| 2007/0287831 | A1 | 12/2007 | Seth et al. |
| 2008/0039618 | A1 | 2/2008 | Allerson et al. |
| 2008/0261905 | A1 | 10/2008 | Herdewijn et al. |
| 2009/0326042 | A1 | 12/2009 | Bhanot et al. |
| 2010/0021914 | A1 | 1/2010 | Moller |
| 2010/0113284 | A1 | 5/2010 | Aristarkhov et al. |
| 2010/0125099 | A1 | 5/2010 | Thoen et al. |
| 2012/0059042 | A1* | 3/2012 | Platenburg et al. ........ 514/44 A |

FOREIGN PATENT DOCUMENTS

| | | |
|---|---|---|
| WO | WO 2007/134181 | 11/2007 |
| WO | WO 2008/042973 | 4/2008 |
| WO | WO 2008/101157 | 8/2008 |
| WO | WO 2008/131807 | 11/2008 |
| WO | WO 2008/154401 | 12/2008 |

OTHER PUBLICATIONS

Saleh et al., Overview of alternative oligonucleotide chemistries for exon skipping, 2012, Exon Skipping: Methods and Protocols, Methods in Molecular Biology, vol. 867, pp. 365-378.*

Aartsma-Rus et al, "Antisense-mediated exon skipping: A versatile tool with therapeutic and research applications" RNA (2007) 13:1609-1624.

Aartsma-Rus et al, "Comparative analysis of antisense oligonucleotide analogs for targeted DMD exon 46 skipping in muscle cells" Gene Therapy (2004) 11:1391-1398.

Akinc et al., "A combinatorial library of lipid-like materials for delivery of RNAi therapeutics" Nature Biotechnology (2008) 26(5):561-569.

Albaek et al., "Bi- and Tricyclic Nucleoside Derivatives Restricted in S-Type Conformations and Obtained by RCM-Reactions" Nucleosides, Nucleotides & Nucleic Acids (2003) 22(5-8):723-725.

Arechavala-Gomeza et al, "Comparitive Analysis of Antisense Oligonucleotide Sequences for Targeted Skipping of Exon 51 During Dystrohin Pre-mRNA Splicing in Human Muscle", Human Gene Therapy (2007) 18:798-810.

Braasch et al., "Locked nucleic acid (LNA): fine-tuning the recognition of DNA and RNA" Chem. Biol. (2001) 8:1-7.

Crooke et al., "Pharmacokinetic Properties of Several Novel Oligonucleotide Analogs in Mice" J. Pharmacol. Exp. Ther. (1996) 277(2):923-937.

Elayadi et al., "Application of PNA and LNA oligomers to chemotherapy" Curr. Opinion Invens. Drugs (2001) 2:558-561.

Englisch et al., "Chemically Modified Oligonucleotides as Probes and Inhibitors" Agnew Chem. Int. Ed. Engl. (1991) 30:613-629.

Freier et al., "The ups and downs of nucleic acid duplex stability: structure-stability studies on chemically-modified DNA:RNA duplexes" Nucleic Acids Research (1997) 25(22):4429-4443.

Frieden et al., "Expanding the design horizon of antisense oligonucleotides with alpha-L-LNA" Nucleic Acids Research (2003) 31(21):6365-6372.

Hua et al., "Antisense Masking of an hnRNP A1/A2 Intronic Splicing Silencer Corrects SMN2 Splicing in Transgenic Mice" The American Journal of Human Genetics (2008) 82:834-848.

Kabanov et al., "A new class of antivirals: antisense oligonucleotides combined with a hydrophobic substituent effectively inhibit influenza virus reproduction and synthesis of virus-specific proteins in MDCK cells" FEBS Lett. (1990) 259:327-330.

Kole et al, "RNA Modulation, Repair and Remodeling by Splice Switching Oligonucleotides", Acta Biochemica Polonica, (2004) 51:373-378.

Koshkin et al., "LNA (locked nucleic acids): Synthesis of the adenine, cytosine, guanine, 5-methylcytosine, thymine and uracil bicyclonucleoside monomers, oligomerisation, and unprecedented nucleic acid recognition" Tetrahedron (1998) 54:3607-3630.

Kroschwitz, "Polynucleotides" Concise Encyclopedia of Polymer Science and Engineering (1990) John Wiley & Sons, Ny pp. 858-859.

Kumar et al., "The first analogues of LNA (locked nucleic acids): phosphorothioate-LNA and 2'-thio-LNA" Bioorg Med Chem Lett. (1998) 8:2219-2222.

Laufer et al, "Noncovalent Peptide-Mediated Delivery of Chemically Modified Steric Block Oligonucleotides Promotes Splice Correction: Quantatative Analysis of Uptake and Biological Effect", Oligonucleotides (2009) 19:63-80.

Letsinger et al., "Cholesteryl-conjugated oligonucleotides: Synthesis, properties, and activity as inhibitors of replication of human immunodeficiency virus in cell culture" PNAS (1989) 86:6553-6556.

Leumann, "DNA analogues: from supramolecular principles to biological properties" Bioorganic & medicinal chemistry (2002) 10(4):841-854.

Manoharan et al., "Cholic Acid-Oligonucleotide Conjugates for Antisense Applications" Bioorg. Med. Chem. Lett. (1994) 4(8):1053-1060.

Manoharan et al., "Chemical Modifications to Improve Uptake and Bioavailability of Antisense Oligonucleotides" Ann. N.Y. Acad. Sci. (1992) 660:306-309.

Manoharan eta 1., "Introduction of a Lipophilic Thioether Tether in the Minor Groove of Nucleic Acids for Antisense Applications" Bioorg. Med. Chem. Lett. (1993) 3(12):2765-2770.

Mishra et al., "Improved leishmanicidal effect of phosphorothioate antisense oligonuceotides by LDL-mediated delivery" Biochim. Biophys. Acta (1995) 1264:229-237.

Oberhauser et al., "Effective incorporation of 2'-O-methyl-oligoribonucleotides into liposomes and enhanced cell association through modification with thiocholesterol" Nucl. Acids Res. (1992) 20(3):533-538.

Orum et al., "Locked nucleic acids: A promising molecular family for gene-function analysis and antisense drug development" Curr. Opinion Mol. Ther. (2001) 3:239-243.

Reichman et al., "The RNA Binding Protein Nuclear Factor 90 Functions as Both a Positive and Negative Regulator of Gene Expression in Mammalian Cells" Mol. Cell Biol. (2002) 22(1):343-356.

Rigo et al, "Synthetic oligonucleotides recruit ILF2/3 to RNA transcripts to modulate splicing" Nature Chemical Biology (2012) 8:555-561.

Saison-Behmoaras et al., "Short modified antisense oligonucleotides directed against Ha-ras point mutation induce selective cleavage of the RNA and inhibit T24 cells proliferation" EMBO J. (1991) 10(5):1111-1118.

Singh et al., "LNA (locked nucleic acids): synthesis and high-affinity nucleic acid recognition" Chem. Commun. (1998) 455-456.

Singh et al., "Synthesis of 2'-amino-LNA: A novel conformationally restricted high-affinity oligonucleotide analogue with a handle" J. Org. Chem. (1998) 63: 10035-10039.

Srivastava et al., "Five- and Six-Membered Conformationally Locked 2',4'-Carbocyclic ribo-Thymidines: Synthesis, Structure, and Biochemical Studies" J. Am. Chem. Soc. (2007) 129(26):8362-8379.

Surono et al, "Chimeric RNA/Ethylene-bridge nucleic acids promote dystrophin expression in myocytes of duchenne muscular dystrophy by inducing skipping of the nonsense mutation-encoding exon", Hluman Gene Therapy (2004) 15:749-757.

Svinarchuk et al., "Inhibition of HIV proliferation in MT-4 cells by antisense oligonucleotide conjugated to lipophilic groups" Biochimie (1993) 75:49-54.

Wahlestedt et al., "Potent and nontoxic antisense oligonucleotide containing locked nucleic acids" Proc. Natl. Acad. Sci. USA (2000) 97: 5633-5638.

Wilton et al, "Spliced Modification to Restore Functional Dystrophin Synthesis in Duchenne Muscular Dystrophy", Current Pharmaceutical Design (2010) 16:988-1001.

Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74:118-134.

(56) References Cited

OTHER PUBLICATIONS

International Search Report for application PCT/US11/40581 dated Nov. 7, 2011.
Lennox et al., "A Direct Comparison of Anti-microRNA Oligonucleotide Potency" Pharmaceutical Research (2010) 27:1788-1799.
Jirka, S. et al., "Evaluation of 2'-Deoxy-2'-fluoro Antisense Oligonucleotides for Exon Skipping in Duchenne Muscular Dystrophy," Molecular Therapy—Nucleic Acids (2015) 4, e265 (8 pages).
Monia, B. et al., "Evaluation of 2'-Modified Oligonucleotides Containing 2'-Deoxy Gaps as Antisense Inhibitors of Gene Expression," Journal of Biological Chemistry, (1993) 268:19, pp 14514-14522.

* cited by examiner

SEQUENCE LISTING

<160> NUMBER OF SEQ ID NOS: 27

<210> SEQ ID NO 1
<211> LENGTH: 18
<212> TYPE: DNA
<213> ORGANISM: Artificial Sequence
<220> FEATURE:
<223> OTHER INFORMATION: Synthetic Oligonucleotide

```
<400> SEQUENCE: 1
atagatatag atagctat                                                 18

<210> SEQ ID NO 2
<211> LENGTH: 18
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: 1, 3-17
<223> OTHER INFORMATION: bases at these positions are RNA

<400> SEQUENCE: 2
atagauauag auagcuat                                                 18

<210> SEQ ID NO 3
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 3
tcactttcat aatgctgg                                                 18

<210> SEQ ID NO 4
<211> LENGTH: 18
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (2)...(18)
<223> OTHER INFORMATION: bases at these positions are RNA

<400> SEQUENCE: 4
tcacuuucau aaugcugg                                                 18

<210> SEQ ID NO 5
<211> LENGTH: 18
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)...(18)
<223> OTHER INFORMATION: bases at these positions are RNA

<400> SEQUENCE: 5
ttaguuuaau cacgcucg                                                 18

<210> SEQ ID NO 6
<211> LENGTH: 18
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (2)...(18)
<223> OTHER INFORMATION: bases at these positions are RNA

<400> SEQUENCE: 6
tcauuugcuu cauacagg                                                 18
```

```
<210> SEQ ID NO 7
<211> LENGTH: 18
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (2)...(28)
<223> OTHER INFORMATION: bases at these positions are RNA

<400> SEQUENCE: 7
tcacuuucau aaugcugg                                                 18

<210> SEQ ID NO 8
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 8
ctttcataat gctggcag                                                 18

<210> SEQ ID NO 9
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 9
ttcactttca taatgctg                                                 18

<210> SEQ ID NO 10
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 10
gattcacttt cataatgc                                                 18

<210> SEQ ID NO 11
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 11
aaagtaagat tcactttc                                                 18

<210> SEQ ID NO 12
<211> LENGTH: 18
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: 1, 3-18
<223> OTHER INFORMATION: bases at these positions are RNA

<400> SEQUENCE: 12
ctuucauaau gcuggcag                                                 18
```

```
<210> SEQ ID NO 13
<211> LENGTH: 18
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: 3-16, 18
<223> OTHER INFORMATION: bases at these positions are RNA

<400> SEQUENCE: 13
ttcacuuuca uaaugctg                                                18

<210> SEQ ID NO 14
<211> LENGTH: 18
<212> TYPE: RNA
<213> ORGANISM: Artificial Sequence
<220> FEATURE:
<223> OTHER INFORMATION: Synthetic Oligonucleotide

<400> SEQUENCE: 14
gauucacuuu cauaaugc                                                18

<210> SEQ ID NO 15
<211> LENGTH: 18
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: 1-16, 18
<223> OTHER INFORMATION: bases at these positions are RNA

<400> SEQUENCE: 15
aaaguaagau ucacuutc                                                18

<210> SEQ ID NO 16
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 16
tccagggagc cgctgccg                                                18

<210> SEQ ID NO 17
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 17
attccaggga gccgctgc                                                18

<210> SEQ ID NO 18
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 18
ggcattccag ggagccgc                                                18
```

```
<210> SEQ ID NO 19
<211> LENGTH: 18
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (2)...(18)
<223> OTHER INFORMATION: bases at these positions are RNA

<400> SEQUENCE: 19
tccagggagc cgcugccg                                                 18

<210> SEQ ID NO 20
<211> LENGTH: 18
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: 1, 3-18
<223> OTHER INFORMATION: bases at these positions are RNA

<400> SEQUENCE: 20
atuccaggga gccgcugc                                                 18

<210> SEQ ID NO 21
<211> LENGTH: 18
<212> TYPE: RNA
<213> ORGANISM: Artificial Sequence
<220> FEATURE:
<223> OTHER INFORMATION: Synthetic Oligonucleotide

<400> SEQUENCE: 21
ggcauuccag ggagccgc                                                 18

<210> SEQ ID NO 22
<211> LENGTH: 23
<212> TYPE: RNA
<213> ORGANISM: Artificial Sequence
<220> FEATURE:
<223> OTHER INFORMATION: Synthetic Oligonucleotide

<400> SEQUENCE: 22
cugccagcau uaugaaagug aau                                           23

<210> SEQ ID NO 23
<211> LENGTH: 18
<212> TYPE: RNA
<213> ORGANISM: Artificial Sequence
<220> FEATURE:
<223> OTHER INFORMATION: Synthetic Oligonucleotide

<400> SEQUENCE: 23
ucacuuucau aaugcugg                                                 18

<210> SEQ ID NO 24
<211> LENGTH: 18
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (2)...(18)
<223> OTHER INFORMATION: bases at these positions are RNA
```

```
<400> SEQUENCE: 24
tcacuuucau aaugcugg                                            18

<210> SEQ ID NO 25
<211> LENGTH: 18
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: 1-4, 7-18
<223> OTHER INFORMATION: bases at these positions are RNA

<400> SEQUENCE: 25
ucacttucau aaugcugg                                            18

<210> SEQ ID NO 26
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 26
tcactttcat aatgctgg                                            18

<210> SEQ ID NO 27
<211> LENGTH: 33
<212> TYPE: RNA
<213> ORGANISM: Artificial Sequence
<220> FEATURE:
<223> OTHER INFORMATION: Synthetic Oligonucleotide

<400> SEQUENCE: 27
aagaguaagu cugccagcau uaugaaagug aau                           33
```

COMPOUNDS AND METHODS FOR MODULATING INTERACTION BETWEEN PROTEINS AND TARGET NUCLEIC ACIDS

CROSS REFERENCED TO RELATED APPLICATIONS

This application is a U.S. National Phase filing under 35 U.S.C. §371 claiming priority to International Serial No. PCT/US2011/040581 filed Jun. 15, 2011, which claims priority to U.S. Provisional Application 61/355,125, filed Jun. 15, 2010, each of which is incorporated herein by reference in its entirety.

SEQUENCE LISTING

The present application is being filed along with a Sequence Listing in electronic format. The Sequence Listing is provided as a file entitled CORE0092USASEQ.TXT, created Dec. 10, 2012, which is 8 Kb in size. The information in the electronic format of the sequence listing is incorporated herein by reference in its entirety.

BACKGROUND OF THE INVENTION

Antisense compounds have been used to modulate target nucleic acids. Antisense compounds comprising a variety of chemical modifications and motifs have been reported. In certain instances, such compounds are useful as research tools, diagnostic reagents, and as therapeutic agents. In certain instances antisense compounds have been shown to modulate protein expression by binding to a target messenger RNA (mRNA) encoding the protein. In certain instances, such binding of an antisense compound to its target mRNA results in cleavage of the mRNA. Antisense compounds that modulate processing of a pre-mRNA have also been reported. Such antisense compounds alter splicing, interfere with polyadenlyation or prevent formation of the 5'-cap of a pre-mRNA.

SUMMARY OF THE INVENTION

In certain embodiments, provided herein are methods of recruiting one or more non-cleaving nucleic acid binding protein to a target nucleic acid in a cell. Certain such methods comprise contacting the cell with an antisense compound comprising a chemically modified oligonucleotide consisting of 8 to 30 linked nucleosides, wherein at least 6 contiguous nucleosides are recruiting nucleosides. In certain embodiments, such recruiting nucleosides are flanked by duplex stabilizing nucleosides. In certain embodiments, the recruiting nucleosides comprise a 2'-F modification. In certain embodiments, the duplex stabilizing nucleosides comprise a 2'-MOE modification.

In certain embodiments, the invention provides methods of modulating splicing of a pre-mRNA comprising contacting a cell with an antisense compound comprising chemical modifications wherein the resulting pre-mRNA/antisense compound duplex is capable of recruiting a protein and wherein recruitment of the protein results in altered splicing of the pre-mRNA. In certain such embodiments, an exon is excluded.

The present disclosure provides the following non-limiting numbered embodiments:

Embodiment 1: A method of recruiting one or more non-cleaving nucleic acid binding proteins to a target nucleic acid in a cell comprising contacting the cell with an antisense compound comprising a chemically modified oligonucleotide consisting of 8 to 30 linked nucleosides, and having:
a 5'-wing region consisting of 0 to 5 linked duplex stabilizing nucleosides;
a 3'-wing region consisting of 0 to 5 linked duplex stabilizing nucleosides; and
a central gap region located between the 5'-wing region and the 3'-wing region and consisting of 5 to 30 linked recruiting nucleosides, wherein
the modified sugar moieties of the recruiting nucleosides are different from the sugar moieties of the nucleosides of the 5'-wing region and the 3'-wing region; and wherein
the oligonucleotide has a nucleobase sequence complementary to a target sequence of the target nucleic acid; and thereby recruiting the non-cleaving nucleic acid binding protein to the target nucleic acid.

Embodiment 2: The method of embodiment 1, wherein the 5'-region consists of 1 to 5 linked duplex stabilizing nucleosides.

Embodiment 3: The method of embodiment 1 or 2, wherein the 3'-region consists of 1 to 5 linked duplex stabilizing nucleosides.

Embodiment 4: The method of any of embodiments 1-3, wherein the sugar moieties of the recruiting nucleosides are all the same as one another.

Embodiment 5: The method of embodiment 4, wherein the sugar moieties of the recruiting nucleosides are all substituted sugar moieties.

Embodiment 6: The method of embodiment 5, wherein the sugar moieties of the recruiting nucleosides each comprise a 2'-modification.

Embodiment 7: The method of embodiment 6, wherein the sugar moieties of the recruiting nucleosides each comprise a 2'-F.

Embodiment 8: The method of embodiment 4, wherein the sugar moieties of the recruiting nucleosides are bicyclic sugar moieties.

Embodiment 9: The method of embodiment 8, wherein the bicyclic sugar moieties comprises a 4'-2' bridge.

Embodiment 10: The method of embodiment 9, wherein the 4'-2' bridge is selected from: 4'-$CH_2$-2', 4'-$(CH_2)_2$-2', 4'-$(CH_2)_3$-2'; 4'-$(CH_2)$—O-2'; 4'-$(CH_2)$—S-2; 4'-$(CH_2)_2$—O-2'; 4'-$CH(CH_3)$—O-2'; and 4'-C—H($CH_2OCH_3$)—O-2'.

Embodiment 11: The method of embodiment 10, wherein the 4'-2' bridge is 4'-$CH(CH_3)$—O-2'.

Embodiment 12: The method of embodiment 4, wherein the sugar moieties of the recruiting nucleosides are tetrahydropyran sugar moieties.

Embodiment 13: The method of embodiment 12, wherein the sugar moieties of the recruiting nucleosides are F-HNA sugar moieties.

Embodiment 14: The method of any of embodiments 1-13, wherein the duplex stabilizing nucleosides of the 5'-wing region are all the same as one another.

Embodiment 15: The method of any of embodiments 1-14, wherein the duplex stabilizing nucleosides of the 3'-wing region are all the same as one another.

Embodiment 16: The method of any of embodiments 1-15, wherein the duplex stabilizing nucleosides of the 5'-wing region and the nucleosides of the 3'-wing region are all the same as one another.

Embodiment 17: The method of embodiment 16, wherein the duplex stabilizing nucleosides are all 2'-MOE nucleosides.

Embodiment 18: The method of any of embodiments 1-17 comprising at least one modified internucleoside linkage.

Embodiment 19: The method of embodiment 18, wherein the at least one modified internucleoside linkage is a phosphorothioate linkage.

Embodiment 20: The method of embodiment 19, wherein each internucleoside linkage is a phosphorothioate linkage.

Embodiment 21: The method of any of embodiments 1-20, wherein the antisense compound comprises at least one conjugate.

Embodiment 22: The method of any of embodiments 1-20, wherein the antisense compound consists of the oligonucleotide.

Embodiment 23: The method of any of embodiments 1-22, wherein at least one of the one or more non-cleaving nucleic acid binding proteins recruited to the target nucleic acid modulates splicing.

Embodiment 24: The method of embodiment 23, wherein at least one of the one or more non-cleaving nucleic acid binding proteins recruited to the target nucleic acid is a splicing activator.

Embodiment 25: The method of embodiment 23, wherein at least one of the one or more non-cleaving nucleic acid binding proteins recruited to the target nucleic acid is a splicing suppressor.

Embodiment 26: The method of any of embodiments 1-25, wherein at least one of the one or more non-cleaving nucleic acid binding proteins recruited to the target nucleic acid modulates localization of the target nucleic acid in the cell.

Embodiment 27: The method of embodiment 26, wherein binding of at least one of the one or more non-cleaving nucleic acid binding proteins recruited to the target nucleic acid increases in the amount of target nucleic acid in the cytoplasm of the cell.

Embodiment 28: The method of embodiment 26, wherein recruiting of at least one of the one or more non-cleaving nucleic acid binding proteins recruited to the target nucleic acid increases localization of the target nucleic acid in a cellular organelle or sub-organelle.

Embodiment 29: The method of any of embodiments 1-28, wherein the recruiting of the non-cleaving nucleic acid binding protein modulates an interaction between the target nucleic acid and a nucleic acid factor.

Embodiment 30: The method of embodiment 29, wherein the recruiting of the non-cleaving nucleic acid binding protein disrupts an interaction between the target nucleic acid and the nucleic acid factor.

Embodiment 31: The method of embodiment 30, wherein the nucleic acid factor is a splicing factor.

Embodiment 32: The method of embodiment 30, wherein the nucleic acid factor is a splicing suppressor.

Embodiment 33: The method of embodiment 30, wherein the nucleic acid factor is modulates localization of the target nucleic acid in the cell.

Embodiment 34: The method of any of embodiments 1-33, wherein at least one of the one or more non-cleaving nucleic acid binding proteins is Interleukin Enhancer Binding Factor 2.

Embodiment 35: The method of any of embodiments 1-33, wherein at least one of the one or more non-cleaving nucleic acid binding proteins is Interleukin Enhancer Binding Factor 3.

Embodiment 36: The method of any of embodiments 1-35, wherein the target nucleic acid is a target non-coding RNA.

Embodiment 37: The method of any of embodiments 1-35, wherein the target nucleic acid is a target microRNA.

Embodiment 38: The method of any of embodiments 1-35, wherein the target nucleic acid is a target mRNA.

Embodiment 39: The method of any of embodiments 1-35, wherein the target nucleic acid is a target pre-mRNA.

Embodiment 40: The method of embodiment 39, wherein the recruiting of the non-cleaving nucleic acid binding protein to the target nucleic acid results in exclusion of a target exon of the target pre-mRNA.

Embodiment 41: The method of embodiment 39, wherein the recruiting of the non-cleaving nucleic acid binding protein to the target nucleic acid results in enhanced exclusion of a target alternate intron of the target pre-mRNA.

Embodiment 42: The method of any of embodiments 39-41, wherein the target sequence is within an intron.

Embodiment 43: The method of any of embodiments 39-41, wherein the target sequence is within an exon.

Embodiment 44: The method of any of embodiments 39-41, wherein the target sequence is spans an intron/exon junction.

Embodiment 45: The method of any of embodiments 1-44 comprising selecting a sugar modification of the recruiting nucleosides to recruit a pre-selected non-cleaving nucleic acid binding protein.

Embodiment 46: The method of any of embodiments 1-45, wherein the cell is a nerve cell.

Embodiment 47: The method of any of embodiments 1-45, wherein the cell is a liver cell.

Embodiment 48: The method of any of embodiments 1-47, wherein the cell is in vitro.

Embodiment 49: The method of any of embodiments 1-47, wherein the cell is in an animal.

Embodiment 50: The method of embodiment 49, wherein the animal is a human.

Embodiment 51: A method of recruiting one or more non-cleaving nucleic acid binding proteins to a target nucleic acid in a cell comprising contacting the cell with an antisense compound comprising a chemically modified oligonucleotide consisting of 8 to 30 linked nucleosides, wherein at least 6 contiguous nucleosides are recruiting nucleosides.

Embodiment 52: The method of embodiment 51, wherein the chemically modified oligonucleotide includes at least one duplex stabilizing nucleoside.

Embodiment 53: The method of embodiment 52, wherein at least one duplex stabilizing nucleosides is a 2'-MOE nucleoside.

Embodiment 54: The method of embodiment 52, wherein each duplex stabilizing nucleosides is a 2'-MOE nucleoside.

Embodiment 55: The method of any of embodiments 51-53, wherein the sugar moieties of the recruiting nucleosides are all the same as one another.

Embodiment 56: The method of embodiment 55, wherein the sugar moieties of the recruiting nucleosides are all substituted sugar moieties.

Embodiment 57: The method of embodiment 56, wherein the sugar moieties of the recruiting nucleosides each comprise a 2'-modification.

Embodiment 58: The method of embodiment 57, wherein the sugar moieties of the recruiting nucleosides each comprise a 2'-F.

Embodiment 59: The method of embodiment 55, wherein the sugar moieties of the recruiting nucleosides are bicyclic sugar moieties.

Embodiment 60: The method of embodiment 59, wherein the bicyclic sugar moieties comprises a 4'-2' bridge.

Embodiment 61: The method of embodiment 60, wherein the 4'-2' bridge is selected from: 4'-$CH_2$-2', 4'-$(CH_2)_2$-2', 4'-$(CH_2)_3$-2'; 4'-$(CH_2)$—O-2; 4'-$(CH_2)$—S-2; 4'-$(CH_2)_2$—O-2; 4'-$CH(CH_3)$—O-2; and 4'-$CH(CH_2OCH_3)$—O-2'.

Embodiment 62: The method of embodiment 61, wherein the 4'-2' bridge is 4'-$CH(CH_3)$—O-2'.

Embodiment 63: The method of embodiment 55, wherein the sugar moieties of the recruiting nucleosides are tetrahydropyran sugar moieties.

Embodiment 64: The method of embodiment 63, wherein the sugar moieties of the recruiting nucleosides are F-HNA sugar moieties.

Embodiment 65: The method of any of embodiments 51-64 comprising at least one modified internucleoside linkage.

Embodiment 66: The method of embodiment 65, wherein the at least one modified internucleoside linkage is a phosphorothioate linkage.

Embodiment 67: The method of embodiment 66, wherein each internucleoside linkage is a phosphorothioate linkage.

Embodiment 68: The method of any of embodiments 51-67, wherein the antisense compound comprises at least one conjugate.

Embodiment 69: The method of any of embodiments 51-67, wherein the antisense compound consists of the oligonucleotide.

Embodiment 70: The method of any of embodiments 51-69, wherein at least one of the one or more non-cleaving nucleic acid binding proteins recruited to the target nucleic acid modulates splicing.

Embodiment 71: The method of embodiment 70, wherein at least one of the one or more non-cleaving nucleic acid binding proteins recruited to the target nucleic acid is a splicing activator.

Embodiment 72: The method of embodiment 70, wherein at least one of the one or more non-cleaving nucleic acid binding proteins recruited to the target nucleic acid is a splicing suppressor.

Embodiment 73: The method of any of embodiments 51-72, wherein at least one of the one or more non-cleaving nucleic acid binding proteins recruited to the target nucleic acid modulates localization of the target nucleic acid in the cell.

Embodiment 74: The method of embodiment 73, wherein binding of at least one of the one or more non-cleaving nucleic acid binding proteins recruited to the target nucleic acid increases in the amount of target nucleic acid in the cytoplasm of the cell.

Embodiment 75: The method of embodiment 74, wherein recruiting of at least one of the one or more non-cleaving nucleic acid binding proteins recruited to the target nucleic acid increases localization of the target nucleic acid in a cellular organelle or sub-organelle.

Embodiment 76: The method of any of embodiments 51-75, wherein the recruiting of the non-cleaving nucleic acid binding protein modulates an interaction between the target nucleic acid and a nucleic acid factor.

Embodiment 77: The method of embodiment 76, wherein the recruiting of the non-cleaving nucleic acid binding protein disrupts an interaction between the target nucleic acid and the nucleic acid factor.

Embodiment 78: The method of embodiment 77, wherein the nucleic acid factor is a splicing factor.

Embodiment 79: The method of embodiment 77, wherein the nucleic acid factor is a splicing suppressor.

Embodiment 80: The method of embodiment 77, wherein the nucleic acid factor is modulates localization of the target nucleic acid in the cell.

Embodiment 81: The method of any of embodiments 51-80, wherein at least one of the one or more non-cleaving nucleic acid binding proteins is Interleukin Enhancer Binding Factor 2.

Embodiment 82: The method of any of embodiments 51-80, wherein at least one of the one or more non-cleaving nucleic acid binding proteins is Interleukin Enhancer Binding Factor 3.

Embodiment 83: The method of any of embodiments 51-82, wherein the target nucleic acid is a target non-coding RNA.

Embodiment 84: The method of any of embodiments 51-82, wherein the target nucleic acid is a target microRNA.

Embodiment 85: The method of any of embodiments 51-82, wherein the target nucleic acid is a target mRNA.

Embodiment 86: The method of any of embodiments 51-82, wherein the target nucleic acid is a target pre-mRNA.

Embodiment 87: The method of embodiment 86, wherein the recruiting of the non-cleaving nucleic acid binding protein to the target nucleic acid results in exclusion of a target exon of the target pre-mRNA.

Embodiment 88: The method of embodiment 86, wherein the recruiting of the non-cleaving nucleic acid binding protein to the target nucleic acid results in enhanced exclusion of a target alternate intron of the target pre-mRNA.

Embodiment 89: The method of any of embodiments 86-88, wherein the target sequence is within an intron.

Embodiment 90: The method of any of embodiments 86-88, wherein the target sequence is within an exon.

Embodiment 91: The method of any of embodiments 86-88, wherein the target sequence is spans an intron/exon junction.

Embodiment 92: The method of any of embodiments 51-91 comprising selecting a sugar modification of the recruiting nucleosides to recruit a pre-selected non-cleaving nucleic acid binding protein.

Embodiment 93: The method of any of embodiments 51-92, wherein the cell is a nerve cell.

Embodiment 94: The method of any of embodiments 51-92, wherein the cell is a liver cell.

Embodiment 95: The method of any of embodiments 51-94, wherein the cell is in vitro.

Embodiment 96: The method of any of embodiments 51-94, wherein the cell is in an animal.

Embodiment 97: The method of embodiment 96, wherein the animal is a human.

Embodiment 98: The method of any of embodiments 51-99, comprising at least 8 contiguous recruiting nucleosides.

Embodiment 99: The method of any of embodiments 51-99, comprising at least 10 contiguous recruiting nucleosides.

Embodiment 100: The method of any of embodiments 51-99, comprising at least 12 contiguous recruiting nucleosides.

Embodiment 101: The method of any of embodiments 51-99, comprising at least 14 contiguous recruiting nucleosides.

Embodiment 102: The method of any of embodiments 51-99, comprising at least 16 contiguous recruiting nucleosides.

Embodiment 103: The method of any of embodiments 51-99, comprising at least 18 contiguous recruiting nucleosides.

Embodiment 104: The method of any of embodiments 51-99, comprising at least 20 contiguous recruiting nucleosides.

Embodiment 105: The method of any of embodiments 1-104 resulting in exclusion of an exon.

Embodiment 106: The method of any of embodiments 1-105 resulting in enhanced exclusion of an alternate exon.

Embodiment 107: The method of any of embodiments 1-106 resulting in enhanced exclusion of an alternate intron.

Embodiment 108: The method of any of embodiments 1-3 or 5-107 wherein at least two of the recruiting nucleosides have modifications that differ from one another.

Embodiment 109: The method of embodiment 108, wherein at least one recruiting nucleoside is a 2'-F modified nucleoside.

Embodiment 110: The method of embodiment 108 or 109, wherein at least one recruiting nucleoside is a bicyclic nucleoside.

Embodiment 111: The method of embodiment 110, wherein at least one bicyclic nucleoside is a constrained-ethyl nucleoside.

Embodiment 112: A method of inducing exon skipping in a target pre-mRNA in a cell comprising contacting the cell with an antisense compound comprising a chemically modified oligonucleotide consisting of 8 to 30 linked nucleosides; and thereby inducing exon skipping in the pre-mRNA in the cell.

Embodiment 113: The method of embodiment 108, wherein the antisense compound binds to the target pre-mRNA and recruits at least one non-cleaving nucleic acid binding protein to the antisense compound/target pre-mRNA duplex.

Embodiment 114: The method of embodiment 109, wherein at least one of the at least one non-cleaving nucleic acid binding protein recruited to the compound/target pre-mRNA duplex is Interleukin Enhancer Binding Factor 2 or Interleukin Enhancer Binding Factor 3.

Embodiment 115: The method of any of embodiments 112-114, wherein each nucleoside of the oligonucleotide is a modified nucleoside.

Embodiment 116: The method of any of embodiments 112-115, wherein at least one nucleoside comprises a 2'-F modification.

Embodiment 117: The method of any of embodiments 112-115, wherein at least two nucleosides comprise a 2'-F modification.

Embodiment 118: The method of any of embodiments 112-115, wherein at least six nucleosides comprise a 2'-F modification.

Embodiment 119: The method of any of embodiments 112-115, wherein at least ten nucleosides comprise a 2'-F modification.

Embodiment 120: The method of any of embodiments 112-115, wherein at least twelve nucleosides comprise a 2'-F modification.

Embodiment 121: The method of any of embodiments 112-120 comprising at least one bicyclic nucleoside.

Embodiment 122: The method of any of embodiments 112-120 comprising at least one constrained-ethyl modified nucleoside.

Embodiment 123: The method of any of embodiments 112-122, wherein the target pre-mRNA is associated with a disease or disorder.

Embodiment 124: The method of embodiment 123, wherein the target pre-mRNA is Bcl-x.

Embodiment 125: The method of embodiment 123, wherein the disease or disorder is cancer.

Embodiment 126: The method of embodiment 123, wherein the disease or disorder is Duchenne muscular dystrophy.

Embodiment 127: The method of any of embodiment 112-127, wherein the cell is in vitro.

Embodiment 128: The method of any of embodiments 112-127, wherein the cell is in an animal.

Embodiment 129: The method of any of embodiments 112-128 comprising performing an assay to determine whether the exon has been skipped.

Embodiment 130: The method of any of embodiments 112-129 comprising performing an assay to determine whether a protein has been recruited to the antisense compound/target pre-mRNA duplex.

Embodiment 131: The method of embodiment 130 comprising performing an assay to determine the identity of one or more protein recruited to the antisense compound/target pre-mRNA duplex.

Embodiment 132: The method of any of embodiments 112-131, wherein the antisense compound is complementary to an intron of the target pre-mRNA.

Embodiment 133: A method of reducing stability of a target RNA in a cell comprising contacting the cell with an antisense compound comprising a chemically modified oligonucleotide consisting of 8 to 30 linked nucleosides; wherein the antisense compound binds to the target RNA and recruits at least one non-cleaving nucleic acid binding protein to the antisense compound/target RNA duplex; and thereby reducing stability of the RNA in the cell.

Embodiment 134: A method of modulating cellular localization of a target RNA in a cell comprising contacting the cell with an antisense compound comprising a chemically modified oligonucleotide consisting of 8 to 30 linked nucleosides; wherein the antisense compound binds to the target RNA and recruits at least one non-cleaving nucleic acid binding protein to the antisense compound/target RNA duplex; and thereby modulating cellular localization of the RNA in the cell.

Embodiment 135: A method of reducing translation of a target RNA in a cell comprising contacting the cell with an antisense compound comprising a chemically modified oligonucleotide consisting of 8 to 30 linked nucleosides; wherein the antisense compound binds to the target RNA and recruits at least one non-cleaving nucleic acid binding protein to the antisense compound/target RNA duplex; and thereby reducing translation of the RNA in the cell.

Embodiment 136: The method of any of embodiments 133-135, wherein at least one of the at least one non-cleaving nucleic acid binding protein recruited to the compound/target RNA duplex is Interleukin Enhancer Binding Factor 2 or Interleukin Enhancer Binding Factor 3.

Embodiment 137: The method of any of embodiments 133-136, wherein each nucleoside of the oligonucleotide is a modified nucleoside.

Embodiment 138: The method of any of embodiments 133-136, wherein at least one nucleoside comprises a 2'-F modification.

Embodiment 139: The method of any of embodiments 133-137, wherein at least two nucleosides comprise a 2'-F modification.

Embodiment 140: The method of any of embodiments 133-137, wherein at least six nucleosides comprise a 2'-F modification.

Embodiment 141: The method of any of embodiments 133-137, wherein at least ten nucleosides comprise a 2'-F modification.

Embodiment 142: The method of any of embodiments 133-137, wherein at least twelve nucleosides comprise a 2'-F modification.

Embodiment 143: The method of any of embodiments 133-142 comprising at least one bicyclic nucleoside.

Embodiment 144: The method of any of embodiments 133-143 comprising at least one constrained-ethyl modified nucleoside.

Embodiment 145: The method of any of embodiments 133-144, wherein the target RNA is associated with a disease or disorder.

Embodiment 146: The method of embodiment 145, wherein the target RNA is a Bcl-x transcript.

Embodiment 147: The method of embodiment 145, wherein the disease or disorder is cancer.

Embodiment 148: The method of any of embodiment 133-147, wherein the cell is in vitro.

Embodiment 149: The method of any of embodiments 133-147, wherein the cell is in an animal.

Embodiment 150: The method of any of embodiments 133-149 comprising performing an assay to determine whether a protein has been recruited to the antisense compound/target RNA duplex.

Embodiment 151: The method of any of embodiments 133-150 comprising performing an assay to determine the identity of one or more protein recruited to the antisense compound/target RNA duplex.

Embodiment 152: The method of any of embodiments 133-151 comprising performing an assay to determine whether stability of the target RNA has been reduced.

Embodiment 153: The method of any of embodiments 133-152 comprising performing an assay to determine whether cellular localization of the target RNA has been modulated.

Embodiment 154: The method of any of embodiments 133-153 comprising performing an assay to determine whether translation of the target RNA has been reduced.

Embodiment 155: The method of any of embodiments 133-154, wherein the target RNA is a target mRNA.

In certain embodiments, including but not limited to any of the above numbered embodiments, an oligomeric compound hybridizes with a target nucleic acid to form a duplex, which in turn binds a protein. In certain embodiments, that protein effects a change. In certain embodiments, the recruited protein effects a change by virtue of its catalytic activity, by its ability to interact with other molecules or by other property of the recruited protein. In certain embodiments, the recruited protein does not directly affect a change, but blocks an interaction that would otherwise occur, thereby effecting a change. In certain embodiments, the change is a modulation of splicing, cellular localization, translation, or transcription. In certain embodiments, the recruited protein disrupts association with a microRNA.

DETAILED DESCRIPTION OF THE INVENTION

Figure 1:
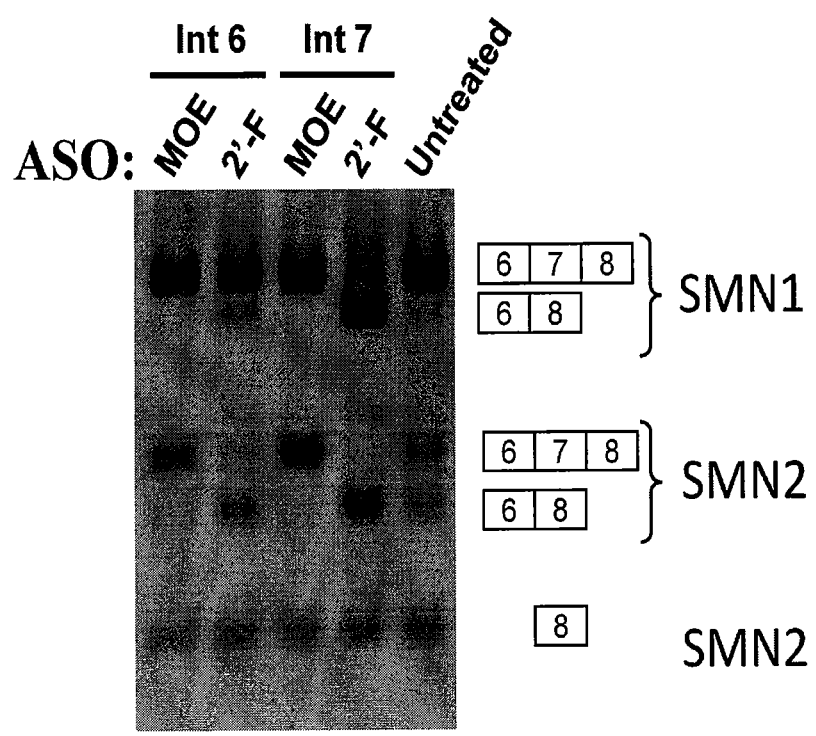
FIG. 1 shows the effect of antisense oligonucleotides having different 2'-modified nucleosides on splicing of SMN1 and SMN2 in HeLa cells as described in Example 1. In untreated cells, exon 7 is mostly retained in SMN1 and mostly skipped in SMN2. Treatment with a full 2'-MOE antisense results in nearly complete exon 7 retention in both SMN1 and SMN2. Treatment with an antisense compound having the identical base sequence, but where all but the two terminal 2'-MOEs on each end are changed to 2'-F has the opposite effect: exon 7 is skipped in both SMN1 and SMN2.

Unless specific definitions are provided, the nomenclature used in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Certain such techniques and procedures may be found for example in "Carbohydrate Modifications in Antisense Research" Edited by Sangvi and Cook, American Chemical Society, Washington D.C., 1994; "Remington's Pharmaceutical Sciences," Mack Publishing Co., Easton, Pa., 18th edition, 1990; and "Antisense Drug Technology, Principles, Strategies, and Applications" Edited by Stanley T. Crooke, CRC Press, Boca Raton, Fla.; and Sambrook et al., "Molecular Cloning, A laboratory Manual," $2^{nd}$ Edition, Cold Spring Harbor Laboratory Press, 1989, which are hereby incorporated by reference for any purpose. Where permitted, all patents, applications, published applications and other publications and other data referred to throughout in the disclosure herein are incorporated by reference in their entirety.

Unless otherwise indicated, the following terms have the following meanings:

As used herein, "nucleoside" means a compound comprising a nucleobase moiety and a sugar moiety. Nucleosides include, but are not limited to, naturally occurring nucleosides (as found in DNA and RNA) and modified nucleosides. Nucleosides may be linked to a phosphate moiety.

As used herein, "chemical modification" means a chemical difference in a compound when compared to a naturally occurring counterpart. In reference to an oligonucleotide, chemical modification does not include differences only in nucleobase sequence. Chemical modifications of oligoncleotides include nucleoside modifications (including sugar moiety modifications and nucleobase modifications) and internucleoside linkage modifications.

As used herein, "furanosyl" means a structure comprising a 5-membered ring comprising four carbon atoms and one oxygen atom.

As used herein, "naturally occurring sugar moiety" means a ribofuranosyl as found in naturally occurring RNA or a deoxyribofuranosyl as found in naturally occurring DNA.

As used herein, "sugar moiety" means a naturally occurring sugar moiety or a modified sugar moiety of a nucleoside.

As used herein, "modified sugar moiety" means a substituted sugar moiety or a sugar surrogate.

As used herein, "substituted sugar moiety" means a furanosyl that is not a naturally occurring sugar moiety. Substituted sugar moieties include, but are not limited to furanosyls comprising modifications at the 2'-position, the 5'-position and/or the 4'-position. Certain substituted sugar moieties are bicyclic sugar moieties.

As used herein, "MOE" means —OCH$_2$CH$_2$OCH$_3$.

As used herein the term "sugar surrogate" means a structure that does not comprise a furanosyl and that is capable of replacing the naturally occurring sugar moiety of a nucleoside, such that the resulting nucleoside is capable of (1) incorporation into an oligonucleotide and (2) hybridization to a complementary nucleoside. Such structures include relatively simple changes to the furanosyl, such as rings comprising a different number of atoms (e.g., 4, 6, or 7-membered rings); replacement of the oxygen of the furanosyl with a non-oxygen atom (e.g., carbon, sulfur, or nitrogen); or both a change in the number of atoms and a replacement of the oxygen. Such structures may also comprise substitutions corresponding with those described for substituted sugar moieties (e.g., 6-membered carbocyclic bicyclic sugar surrogates optionally comprising additional substituents). Sugar surrogates also include more complex sugar replacements (e.g., the non-ring systems of peptide nucleic acid). Sugar surrogates include without limitation morpholinos, cyclohexenyls and cyclohexitols.

As used herein, "bicyclic sugar moiety" means a modified sugar moiety comprising a 4 to 7 membered ring (including but not limited to a furanosyl) comprising a bridge connecting two atoms of the 4 to 7 membered ring to form a second ring, resulting in a bicyclic structure. In certain embodiments, the 4 to 7 membered ring is a sugar ring. In certain embodiments the 4 to 7 membered ring is a furanosyl. In certain such embodiments, the bridge connects the 2'-carbon and the 4'-carbon of the furanosyl.

As used herein, "nucleotide" means a nucleoside further comprising a phosphate linking group. As used herein, "linked nucleosides" may or may not be linked by phosphate linkages and thus includes, but is not limited to "linked nucleotides."

As used herein, "nucleobase" means group of atoms that can be linked to a sugar moiety to create a nucleoside that is capable of incorporation into an oligonucleotide, and wherein the group of nucleobase atoms are capable of bonding with a complementary nucleobase of another oligonucleotide or nucleic acid. Nucleobases may be naturally occurring or may be modified.

As used herein, "heterocyclic base" or "heterocyclic nucleobase" means a nucleobase comprising a heterocyclic structure.

As used herein the terms, "unmodified nucleobase" or "naturally occurring nucleobase" means the naturally occurring heterocyclic nucleobases of RNA or DNA: the purine bases adenine (A) and guanine (G), and the pyrimidine bases thymine (T), cytosine (C) (including 5-methyl C), and uracil (U).

As used herein, "modified nucleobase" means any nucleobase that is not an unmodified nucleobase.

As used herein, "modified nucleoside" means a nucleoside comprising at least one chemical modification compared to naturally occurring RNA or DNA nucleosides. Modified nucleosides comprise a modified sugar moiety and/or a modified nucleobase.

As used herein, "bicyclic nucleoside" or "BNA" means a nucleoside comprising a bicyclic sugar moiety.

As used herein, "oligonucleotide" means a compound comprising a plurality of linked nucleosides. In certain embodiments, an oligonucleotide comprises one or more unmodified ribonucleosides (RNA) and/or unmodified deoxyribonucleosides (DNA) and/or one or more modified nucleosides.

As used herein "oligonucleoside" means an oligonucleotide in which none of the internucleoside linkages contains a phosphorus atom. As used herein, oligonucleotides include oligonucleosides.

As used herein, "modified oligonucleotide" means an oligonucleotide comprising at least one modified nucleoside and/or at least one modified internucleoside linkage.

As used herein "internucleoside linkage" means a covalent linkage between adjacent nucleosides in an oligonucleotide.

As used herein "naturally occurring internucleoside linkage" means a 3' to 5' phosphodiester linkage.

As used herein, "modified internucleoside linkage" means any internucleoside linkage other than a naturally occurring internucleoside linkage.

As used herein, "oligomeric compound" means a polymeric structure comprising two or more sub-structures. In certain embodiments, an oligomeric compound comprises an oligonucleotide. In certain embodiments, an oligomeric compound comprises one or more conjugate groups and/or terminal groups. In certain embodiments, an oligomeric compound consists of an oligonucleotide.

As used herein, the term "double-stranded" in reference to a compound or composition means two separate oligomeric compounds that are hybridized to one another. Double-stranded oligomeric compounds may include one or more non-hybridizing nucleosides at one or both ends of one or both strands (overhangs) and/or one or more internal non-hybridizing nucleosides (mismatches) provided there is sufficient complementarity to maintain hybridization under relevant conditions. In certain embodiments, a double-stranded oligomeric compound may become single-stranded after contacting a cell or enzyme within a cell.

As used herein, the term "self-complementary" or "hair-pin" in reference to an oligomeric compound means a single oligomeric compound that comprises a stable duplex region formed by the oligomeric compound hybridizing to itself. In certain embodiments, the stable duplex region of a hair-pin oligomeric compound comprises at least 5 contiguous paired nucleobases. In certain embodiments, the stable duplex region of a hair-pin oligomeric compound comprises at least 6 contiguous paired nucleobases. In certain embodiments, the stable duplex region of a hair-pin oligomeric compound comprises at least 7 contiguous paired nucleobases. In certain embodiments, the duplex region of a hair-pin compound constitutes ≥70% of the total number of nucleobases of the hair-pin compound.

As used herein, the term "single-stranded" means an oligomeric compound that is not hybridized to its complement and that is not a hair-pin oligomeric compound. Typically, single-stranded compounds are capable of binding to their complementary strands to become double-stranded or partially double-stranded compounds.

As used herein, "terminal group" means one or more atom attached to either, or both, the 3' end or the 5' end of an oligonucleotide. In certain embodiments a terminal group is a conjugate group. In certain embodiments, a terminal group comprises one or more terminal group nucleosides.

As used herein, "conjugate" means an atom or group of atoms bound to an oligonucleotide or oligomeric compound. In general, conjugate groups modify one or more properties of the compound to which they are attached, including, but not limited to pharmacodynamic, pharmacokinetic, binding, absorption, cellular distribution, cellular uptake, charge and clearance.

As used herein, "conjugate linking group" means any atom or group of atoms used to attach a conjugate to an oligonucleotide or oligomeric compound.

As used herein, "antisense compound" means a compound comprising or consisting of an oligonucleotide at least a portion of which is at least partially complementary to a target nucleic acid to which it is capable of hybridizing, resulting in at least one antisense activity.

As used herein, "antisense activity" means any detectable and/or measurable change attributable to the hybridization of an antisense compound to its target nucleic acid.

As used herein, "detecting" or "measuring" means that a test or assay for detecting or measuring is performed. Such detection and/or measuring may result in a value of zero. Thus, if a test for detection or measuring results in a finding of no activity (activity of zero), the step of detecting or measuring the activity has nevertheless been performed.

As used herein, "detectable and/or measureable activity" means an activity that is not zero.

As used herein, "essentially unchanged" means little or no change in a particular parameter, particularly relative to another parameter which changes much more. In certain embodiments, a parameter is essentially unchanged when it changes less than 5%. In certain embodiments, a parameter is essentially unchanged if it changes less than two-fold while another parameter changes at least ten-fold. For example, in certain embodiments, an antisense activity is a change in the amount of a target nucleic acid. In certain such embodiments, the amount of a non-target nucleic acid is essentially unchanged if it changes much less than the target nucleic acid does, but need not be zero.

As used herein, "expression" means the process by which a gene ultimately results in a protein. Expression includes, but is not limited to, transcription, post-transcriptional modification (e.g., splicing, polyadenlyation, addition of 5'-cap), and translation.

As used herein, "recruit" means to bring molecules into association where they would not otherwise be in association. Thus, an oligonucleotide that recruits a protein to a target region of a target nucleic acid causes the protein to become in association with the target region of the target nucleic acid where the protein would not otherwise be in association with that region of that nucleic acid. An oligonucleotide capable of recruiting a protein does not include an oligonucleotide to which a protein has been covalently bound.

As used herein, "recruited protein" means a protein that becomes associated with an antisense compound/target nucleic acid duplex. Typically, recruited proteins are endogenous cellular proteins.

As used herein, "recruiting nucleoside" means a modified nucleoside which, when incorporated into an oligonucleotide is capable of recruiting a protein. In certain embodiments, a contiguous region of 4 recruiting nucleosides is required for recruitment. In certain embodiments, a contiguous region of 5 recruiting nucleosides is required for recruitment. In certain embodiments, a contiguous region of 6 recruiting nucleosides is required for recruitment. In certain embodiments, a contiguous region of 7 recruiting nucleosides is required for recruitment. In certain embodiments, a contiguous region of 8 recruiting nucleosides is required for recruitment.

As use herein, "high affinity nucleoside" means a nucleoside which, when incorporated into an oligonucleotide, increases the affinity of the oligonucleotide for a nucleic acid target, compared to an unmodified nucleoside.

As used herein, "stabilizing nucleoside" means a nucleoside that is resistant to degradation, including, but not limited to nuclease degradation, compared to unmodified nucleases.

As used herein, "duplex stabilizing nucleoside" means a nucleoside that is either a high affinity nucleoside or stabilizing nucleoside or both a high affinity nucleoside and stabilizing nucleoside.

As used herein, "non-cleaving nucleic acid binding protein" means a protein capable of being recruited to a target nucleic acid/oligonucleotide duplex that does not cleave either strand of that duplex. RNase H and Ago2 are not non-cleaving nucleic acid binding proteins.

As used herein, "target nucleic acid" means a nucleic acid molecule to which an antisense compound hybridizes.

As used herein, "mRNA" means an RNA molecule that encodes a protein.

As used herein, "pre-mRNA" means an RNA transcript that has not been fully processed into mRNA. Pre-RNA includes one or more intron.

As used herein, "exon" means a portion of a pre-mRNA which, after splicing, is typically included in the mature mRNA.

As used herein, "intron" means a portion of a pre-mRNA which, after splicing, is typically excluded in the mature mRNA.

As used herein, "alternative exon" means a portion of a pre-mRNA that is sometimes included and sometimes excluded in the mature mRNA. In certain embodiments the present invention provides methods that result in exclusion of an alternative exon, by which is meant that the amount of exon excluded is increased relative to conditions absent the method. Likewise methods that result in inclusion of an alternative exon increase the amount of that exon included.

As used herein, "alternative intron" means a portion of a pre-mRNA that is sometimes included and sometimes excluded in the mature mRNA. In certain embodiments the present invention provides methods that result in exclusion of an alternative intron, by which is meant that the amount of intron excluded is increased relative to conditions absent the method. Likewise methods that result in inclusion of an alternative intron increase the amount of that inton included.

As used herein, "pdRNA" means an RNA molecule that interacts with one or more promoter to modulate transcription.

As used herein, "object RNA" means an RNA molecule other than a target RNA, the amount, activity, splicing, and/or function of which is modulated, either directly or indirectly, by a target nucleic acid. In certain embodiments, a target nucleic acid modulates splicing of an object RNA. In certain such embodiments, an antisense compound modulates the amount or activity of the target nucleic acid, resulting in a change in the splicing of object RNA and ultimately resulting in a change in the activity or function of the object RNA.

As used herein, "microRNA" means a naturally occurring, small, non-coding RNA that represses gene expression of at least one mRNA. In certain embodiments, a microRNA represses gene expression by binding to a target site within a 3' untranslated region of an mRNA. In certain embodiments, a microRNA has a nucleobase sequence as set forth in miRBase, a database of published microRNA sequences found at microrna.sanger.ac.uk/sequences/. In certain embodiments, a microRNA has a nucleobase sequence as set forth in miRBase version 12.0 released September 2008, which is herein incorporated by reference in its entirety.

As used herein, "microRNA mimic" means an oligomeric compound having a sequence that is at least partially identical to that of a microRNA. In certain embodiments, a microRNA mimic comprises the microRNA seed region of a microRNA. In certain embodiments, a microRNA mimic modulates translation of more than one target nucleic acids. In certain embodiments, a microRNA mimic is double-stranded.

As used herein, "targeting" or "targeted to" means the association of an antisense compound to a particular target nucleic acid molecule or a particular region of nucleotides within a target nucleic acid molecule. An antisense compound targets a target nucleic acid if it is sufficiently complementary to the target nucleic acid to allow hybridization under physiological conditions.

As used herein, "nucleobase complementarity" or "complementarity" when in reference to nucleobases means a nucleobase that is capable of base pairing with another nucleobase. For example, in DNA, adenine (A) is complementary to thymine (T). For example, in RNA, adenine (A) is complementary to uracil (U). In certain embodiments, complementary nucleobase means a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair. Nucleobases comprising certain modifications may maintain the ability to pair with a counterpart nucleobase and thus, are still capable of nucleobase complementarity.

As used herein, "non-complementary" in reference to nucleobases means a pair of nucleobases that do not form hydrogen bonds with one another or otherwise support hybridization.

As used herein, "complementary" in reference to oligomeric compounds (e.g., linked nucleosides, oligonucleotides, or nucleic acids) means the capacity of such oligomeric compounds or regions thereof to hybridize to another oligomeric compound or region thereof through nucleobase complementarity.

As used herein, "hybridization" means the pairing of complementary oligomeric compounds (e.g., an antisense compound and its target nucleic acid). While not limited to a particular mechanism, the most common mechanism of pairing involves hydrogen bonding, which may be Watson-Crick, Hoogsteen or reversed Hoogsteen hydrogen bonding, between complementary nucleobases.

As used herein, "specifically hybridizes" means the ability of an oligomeric compound to hybridize to one nucleic acid site with greater affinity than it hybridizes to another nucleic acid site. In certain embodiments, an antisense oligonucleotide specifically hybridizes to more than one target site.

As used herein, "fully complementary" in reference to an oligonucleotide or portion thereof means that each nucleobase of the oligonucleotide or portion thereof is capable of pairing with a nucleobase of a complementary nucleic acid or contiguous portion thereof. Thus, fully complementary region comprises no mismatches or unhybridized nucleobases in either strand.

As used herein, "percent complementarity" means the percentage of nucleobases of an oligomeric compound that are complementary to an equal-length portion of a target nucleic acid. Percent complementarity is calculated by dividing the number of nucleobases of the oligomeric compound that are complementary to nucleobases at corresponding positions in the target nucleic acid by the total length of the oligomeric compound.

As used herein, "percent identity" means the number of nucleobases in a first nucleic acid that are the same type (independent of chemical modification) as nucleobases at corresponding positions in a second nucleic acid, divided by the total number of nucleobases in the first nucleic acid.

As used herein, "modulation" means a perturbation of amount or quality of a function or activity when compared to the function or activity prior to modulation. For example, modulation includes the change, either an increase (stimulation or induction) or a decrease (inhibition or reduction) in gene expression. As a further example, modulation of expression can include perturbing splice site selection of pre-mRNA processing, resulting in a change in the amount of a particular splice-variant present compared to conditions that were not perturbed. As a further example, modulation includes perturbing translation of a protein.

As used herein, "motif" means a pattern of chemical modifications in an oligomeric compound or a region thereof. Motifs may be defined by modifications at certain nucleosides and/or at certain linking groups of an oligomeric compound.

As used herein, "nucleoside motif" means a pattern of nucleoside modifications in an oligomeric compound or a region thereof. The linkages of such an oligomeric compound may be modified or unmodified. Unless otherwise indicated, motifs herein describing only nucleosides are intended to be nucleoside motifs. Thus, in such instances, the linkages are not limited.

As used herein, "linkage motif" means a pattern of linkage modifications in an oligomeric compound or region thereof. The nucleosides of such an oligomeric compound may be modified or unmodified. Unless otherwise indicated, motifs herein describing only linkages are intended to be linkage motifs. Thus, in such instances, the nucleosides are not limited.

As used herein, "nucleobase modification motif" means a pattern of modifications to nucleobases along an oligonucleotide. Unless otherwise indicated, a nucleobase modification motif is independent of the nucleobase sequence.

As used herein, "sequence motif" means a pattern of nucleobases arranged along an oligonucleotide or portion thereof. Unless otherwise indicated, a sequence motif is independent of chemical modifications.

As used herein, "type of modification" in reference to a nucleoside or a nucleoside of a "type" means the chemical modification of a nucleoside and includes modified and unmodified nucleosides. Accordingly, unless otherwise indicated, a "nucleoside having a modification of a first type" may be an unmodified nucleoside.

As used herein, "differently modified" mean chemical modifications or chemical substituents that are different from one another, including absence of modifications. Thus, for example, a MOE nucleoside and an unmodified DNA nucleoside are "differently modified," even though the DNA nucleoside is unmodified. Likewise, DNA and RNA are "differently modified," even though both are naturally-occurring unmodified nucleosides. Nucleosides that are the same but for comprising different nucleobases are not differently modified, unless otherwise indicated. For example, a nucleoside comprising a 2'-OMe modified sugar and an unmodified adenine nucleobase and a nucleoside comprising a 2'-OMe modified sugar and an unmodified thymine nucleobase are not differently modified.

As used herein, "the same type of modifications" refers to modifications that are the same as one another, including absence of modifications. Thus, for example, two unmodified DNA nucleoside have "the same type of modification," even though the DNA nucleoside is unmodified. Such nucleosides having the same type modification may comprise different nucleobases.

As used herein, "separate regions" means a portion of an oligonucleotide wherein the chemical modifications or the motif of chemical modifications within the portion are the same and the chemical modifications or motif of chemical modifications of any neighboring portions include at least one difference to allow the separate regions to be distinguished from one another.

As used herein, "pharmaceutically acceptable carrier or diluent" means any substance suitable for use in administering to an animal. In certain embodiments, a pharmaceutically acceptable carrier or diluent is sterile saline. In certain embodiments, such sterile saline is pharmaceutical grade saline.

As used herein, "substituent" and "substituent group," means an atom or group that replaces the atom or group of a named parent compound. For example a substituent of a modified nucleoside is any atom or group that differs from the atom or group found in a naturally occurring nucleoside (e.g., a modified 2'-substituent is any atom or group at the 2'-position of a nucleoside other than H or OH).

Substituent groups can be protected or unprotected. In certain embodiments, compounds of the present invention have substituents at one or at more than one position of the parent compound. Substituents may also be further substituted with other substituent groups and may be attached directly or via a linking group such as an alkyl or hydrocarbyl group to a parent compound.

Likewise, as used herein, "substituent" in reference to a chemical functional group means an atom or group of atoms differs from the atom or a group of atoms normally present in the named functional group. In certain embodiments, a substituent replaces a hydrogen atom of the functional group (e.g., in certain embodiments, the substituent of a substituted methyl group is an atom or group other than hydrogen which replaces one of the hydrogen atoms of an unsubstituted methyl group). Unless otherwise indicated, groups amenable for use as substituents include without limitation, halogen, hydroxyl, alkyl, alkenyl, alkynyl, acyl (—C(O)$R_{aa}$), carboxyl (—C(O)O—$R_{aa}$), aliphatic groups, alicyclic groups, alkoxy, substituted oxy (—O—$R_{aa}$), aryl, aralkyl, heterocylic radical, heteroaryl, heteroarylalkyl, amino (—N($R_{bb}$)—($R_{cc}$), imino(=$NR_{bb}$), amido (—C(O)N($R_{bb}$)($R_{cc}$) or —N($R_{bb}$)C(O)$R_{aa}$), azido (—$N_3$), nitro (—$NO_2$), cyano (—CN), carbamido (—OC(O)N($R_{bb}$)($R_{cc}$) or —N($R_{bb}$)C(O)O$R_{aa}$), ureido (—N($R_{bb}$)C(O)N($R_{bb}$)($R_{cc}$)), thioureido (—N($R_{bb}$)C(S)N($R_{bb}$)($R_{cc}$)), guanidinyl (—N($R_{bb}$)C(=$NR_{bb}$)N($R_{bb}$)($R_{cc}$)), amidinyl (—C(=$NR_{bb}$)N($R_{bb}$)($R_{cc}$) or —N($R_{bb}$)C(=$NR_{bb}$)($R_{aa}$)), thiol (—$SR_{bb}$), sulfinyl (—S(O)$R_{bb}$), sulfonyl (—S(O)$_2R_{bb}$) and sulfonamidyl (—S(O)$_2$N($R_{bb}$)($R_{cc}$) or —N($R_{bb}$)S(O)$_2R_{bb}$). Wherein each $R_{aa}$, $R_{bb}$ and $R_{cc}$ is, independently, H, an optionally linked chemical functional group or a further substituent group with a preferred list including without limitation, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

As used herein, "recursive substituent" means that a substituent may recite another instance of itself. Because of the recursive nature of such substituents, theoretically, a large number may be present in any given claim. One of ordinary skill in the art of medicinal chemistry and organic chemistry understands that the total number of such substituents is reasonably limited by the desired properties of the compound intended. Such properties include, by way of example and not limitation, physical properties such as molecular weight, solubility or log P, application properties such as activity against the intended target and practical properties such as ease of synthesis.

Recursive substituents are an intended aspect of the invention. One of ordinary skill in the art of medicinal and organic chemistry understands the versatility of such substituents. To the degree that recursive substituents are present in a claim of the invention, the total number will be determined as set forth above.

As used herein, "stable compound" and "stable structure" mean a compound that is sufficiently robust to survive isolation to a useful degree of purity from a reaction mixture, and formulation into an therapeutic agent.

As used herein, "alkyl," as used herein, means a saturated straight or branched hydrocarbon radical containing up to twenty four carbon atoms. Examples of alkyl groups include without limitation, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred. The term "lower alkyl" as used herein includes from 1 to about 6 carbon atoms. Alkyl groups as used herein may optionally include one or more further substituent groups.

As used herein, "alkenyl," means a straight or branched hydrocarbon chain radical containing up to twenty four carbon atoms and having at least one carbon-carbon double bond. Examples of alkenyl groups include without limitation, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

As used herein, "alkynyl," means a straight or branched hydrocarbon radical containing up to twenty four carbon atoms and having at least one carbon-carbon triple bond. Examples of alkynyl groups include, without limitation, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

As used herein, "acyl," means a radical formed by removal of a hydroxyl group from an organic acid and has the general Formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

As used herein, "alicyclic" means a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups.

As used herein, "aliphatic" means a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation, polyalkoxys, such as polyalkylene glycols, polyamines, and polyimines. Aliphatic groups as used herein may optionally include further substituent groups.

As used herein, "alkoxy" means a radical formed between an alkyl group and an oxygen atom wherein the oxygen atom is used to attach the alkoxy group to a parent molecule. Examples of alkoxy groups include without limitation, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

As used herein, "aminoalkyl" means an amino substituted $C_1$-$C_{12}$ alkyl radical. The alkyl portion of the radical forms a covalent bond with a parent molecule. The amino group can be located at any position and the aminoalkyl group can be substituted with a further substituent group at the alkyl and/or amino portions.

As used herein, "aralkyl" and "arylalkyl" mean an aromatic group that is covalently linked to a $C_1$-$C_{12}$ alkyl radical. The alkyl radical portion of the resulting aralkyl (or arylalkyl) group forms a covalent bond with a parent molecule. Examples include without limitation, benzyl, phenethyl and the like. Aralkyl groups as used herein may optionally include further substituent groups attached to the alkyl, the aryl or both groups that form the radical group.

As used herein, "aryl" and "aromatic" mean a mono- or polycyclic carbocyclic ring system radicals having one or more aromatic rings. Examples of aryl groups include without limitation, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

As used herein, "halo" and "halogen," mean an atom selected from fluorine, chlorine, bromine and iodine.

As used herein, "heteroaryl," and "heteroaromatic," mean a radical comprising a mono- or poly-cyclic aromatic ring, ring system or fused ring system wherein at least one of the rings is aromatic and includes one or more heteroatoms. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include without limitation, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl and the like. Heteroaryl radicals can be attached to a parent molecule directly or through a linking moiety such as an aliphatic group or hetero atom. Heteroaryl groups as used herein may optionally include further substituent groups.

Oligomeric Compounds

In certain embodiments, the present invention provides oligomeric compounds. In certain embodiments, such oligomeric compounds comprise oligonucleotides optionally comprising one or more conjugate and/or terminal groups. In certain embodiments, oligomeric compounds consist of an oligonucleotide. In certain embodiments, oligonucleotides comprise one or more chemical modification. Such chemical modifications include modifications one or more nucleoside (including modifications to the sugar moiety and/or the nucleobase) and/or modifications to one or more internucleoside linkage.

Certain Sugar Moieties

In certain embodiments, oligomeric compounds of the invention comprise one or more modified nucleoside comprising a modified sugar moiety. Such oligomeric compounds comprising one or more sugar-modified nucleoside may have desirable properties, such as enhanced nuclease stability or increased binding affinity with a target nucleic acid relative to oligomeric compounds comprising only nucleosides comprising naturally occurring sugar moieties. In certain embodiments, modified sugar moieties are substituted sugar moieties. In certain embodiments, modified sugar moieties are sugar surrogates. Such sugar surrogates may comprise one or more substitutions corresponding to those of substituted sugar moieties.

In certain embodiments, modified sugar moieties are substituted sugar moieties comprising one or more non-bridging sugar substituent, including but not limited to substituents at the 2' and/or 5' positions. Examples of sugar substituents suitable for the 2'-position, include, but are not limited to: 2'-F, 2'-OCH$_3$ ("OMe" or "O-methyl"), and 2'-O(CH$_2$)$_2$OCH$_3$ ("MOE"). In certain embodiments, sugar substituents at the 2' position is selected from allyl, amino, azido, thio, O—$C_1$-$C_{10}$ alkyl, O—$C_1$-$C_{10}$ substituted alkyl; OCF$_3$, O(CH$_2$)$_2$SCH$_3$, O(CH$_2$)$_2$—O—N(Rm)(Rn), and O—CH$_2$—C(=O)—N(Rm)(Rn), where each Rm and Rn is, independently, H or substituted or unsubstituted $C_1$-$C_{10}$ alkyl. Examples of sugar substituents at the 5'-position, include, but are not limited to: 5'-methyl (R or S); 5'-vinyl, and 5'-methoxy. In certain embodiments, substituted sugars comprise more than one non-bridging sugar substituent, for example, 2'-F-5'-methyl sugar moieties (see, e.g., PCT International Application WO 2008/101157, for additional 5',2'-bis substituted sugar moieties and nucleosides).

Nucleosides comprising 2'-modified sugar moieties are referred to as 2'-modified nucleosides. In certain embodiments, a 2'-modified nucleoside comprises a 2'-substituent group selected from halo, allyl, amino, azido, SH, CN, OCN, CF$_3$, OCF$_3$, O-, S-, or N(R$_m$)-alkyl; O-, S-, or N(R$_m$)-alkenyl; O-, S- or N(R$_m$)-alkynyl; O-alkylenyl-O-alkyl, alkynyl, alkaryl, aralkyl, O-alkaryl, O-aralkyl, O(CH$_2$)$_2$SCH$_3$, O—(CH$_2$)$_2$—O—N(R$_m$)(R$_n$) or O—CH$_2$—C(=O)—N(R$_m$)(R$_n$), where each R$_m$ and R$_n$ is, independently, H, an amino protecting group or substituted or unsubstituted $C_1$-$C_{10}$ alkyl. These 2'-substituent groups can be further substituted with one or more substituent groups independently selected from hydroxyl, amino, alkoxy, carboxy, benzyl, phenyl, nitro (NO$_2$), thiol, thioalkoxy (S-alkyl), halogen, alkyl, aryl, alkenyl and alkynyl.

In certain embodiments, a 2'-modified nucleoside comprises a 2'-substituent group selected from F, NH$_2$, N$_3$, OCF$_3$, O—CH$_3$, O(CH$_2$)$_3$NH$_2$, CH$_2$—CH=CH$_2$, O—CH$_2$—CH=CH$_2$, OCH$_2$CH$_2$OCH$_3$, O(CH$_2$)$_2$SCH$_3$, O—(CH$_2$)$_2$—O—N(R$_m$)(R$_n$), —O(CH$_2$)$_2$—O—(CH$_2$)$_2$N(CH$_3$)$_2$, and N-substituted acetamide (O—CH$_2$—C(=O)—N(R$_m$)(R$_n$) where each R$_m$ and R$_n$ is, independently, H, an amino protecting group or substituted or unsubstituted $C_1$-$C_{10}$ alkyl.

In certain embodiments, a 2'-modified nucleoside comprises a sugar moiety comprising a 2'-substituent group selected from F, OCF$_3$, O—CH$_3$, OCH$_2$CH$_2$OCH$_3$, 2'-O(CH$_2$)$_2$SCH$_3$, O—(CH$_2$)$_2$—O—N(CH$_3$)$_2$, —O(CH$_2$)$_2$—O—(CH$_2$)$_2$N(CH$_3$)$_2$, and O—CH$_2$—C(=O)—N(H)CH$_3$.

In certain embodiments, a 2'-modified nucleoside comprises a sugar moiety comprising a 2'-substituent group selected from F, O—CH$_3$, and OCH$_2$CH$_2$OCH$_3$.

Certain substituted sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. Examples of such 4' to 2' sugar substituents, include, but are not limited to: —[C(R$_a$)(R$_b$)]$_n$—, —[C(R$_a$)(R$_b$)]$_n$—O—, —C(R$_a$R$_b$)—N(R)—O— or, —C(R$_a$R$_b$)—O—N(R)—; 4'-CH$_2$-2', 4'-(CH$_2$)$_2$-2', 4'-(CH$_2$)$_3$-2', 4'-(CH$_2$)—O-2' (LNA); 4'-(CH$_2$)—S-2; 4'-(CH$_2$)$_2$—O-2' (ENA); 4'-CH(CH$_3$)—O-2' (cEt) and 4'-CH(CH$_2$OCH$_3$)—O-2', and analogs thereof (see, e.g., U.S. Pat. No. 7,399,845, issued on Jul. 15, 2008); 4'-C(CH$_3$)(CH$_3$)—O-2' and analogs thereof, (see, e.g., WO2009/006478, published Jan. 8, 2009); 4'-CH$_2$—N(OCH$_3$)-2' and analogs thereof (see, e.g., WO2008/150729, published Dec. 11, 2008); 4'-CH$_2$—O—N(CH$_3$)-2' (see, e.g., US2004/0171570, published Sep. 2, 2004); 4'-CH$_2$—O—N(R)-2', and 4'-CH$_2$—N(R)—O-2'-, wherein each R is, independently, H, a protecting group, or C$_1$-C$_{12}$ alkyl; 4'-CH$_2$—N(R)—O-2', wherein R is H, C$_1$-C$_{12}$ alkyl, or a protecting group (see, U.S. Pat. No. 7,427,672, issued on Sep. 23, 2008); 4'-CH$_2$—C(H)(CH$_3$)-2' (see, e.g., Chattopadhyaya, et al., *J. Org. Chem.*, 2009, 74, 118-134); and 4'-CH$_2$—C(=CH$_2$)-2' and analogs thereof (see, published PCT International Application WO 2008/154401, published on Dec. 8, 2008).

In certain embodiments, such 4' to 2' bridges independently comprise 1 or from 2 to 4 linked groups independently selected from —[C(R$_a$)(R$_b$)]$_n$—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_a$)—;

wherein:

x is 0, 1, or 2;

n is 1, 2, 3, or 4;

each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl, or a protecting group.

Nucleosides comprising bicyclic sugar moieties are referred to as bicyclic nucleosides or BNAs. Bicyclic nucleosides include, but are not limited to, (A) α-L-Methyleneoxy (4'-CH$_2$—O-2') BNA, (B) β-D-Methyleneoxy (4'-CH$_2$—O-2') BNA, (C) Ethyleneoxy (4'-(CH$_2$)$_2$—O-2') BNA, (D) Aminooxy (4'-CH$_2$—O—N(R)-2') BNA, (E) Oxyamino (4'-CH$_2$—N(R)—O-2') BNA, (F) Methyl(methyleneoxy) (4'-CH(CH$_3$)—O-2') BNA (also referred to as constrained ethyl or cEt), (G) methylene-thio (4'-CH$_2$—S-2') BNA, (H) methylene-amino (4'-CH$_2$—N(R)-2') BNA, (I) methyl carbocyclic (4'-CH$_2$—CH(CH$_3$)-2') BNA, and (J) propylene carbocyclic (4'-(CH$_2$)$_3$-2') BNA as depicted below.

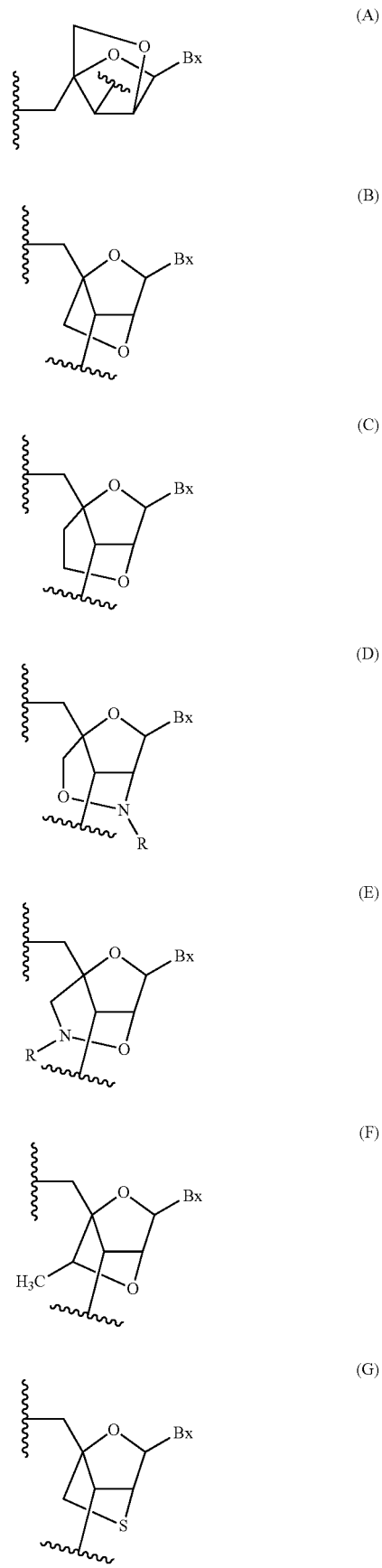

-continued (H)
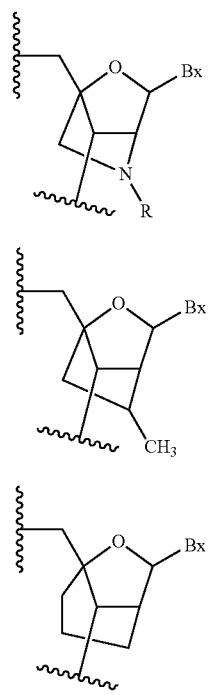

(I)

(J)

wherein Bx is a nucleobase moiety and R is, independently, H, a protecting group, or $C_1$-$C_{12}$ alkyl.

In certain embodiments, bicyclic nucleosides have Formula I:

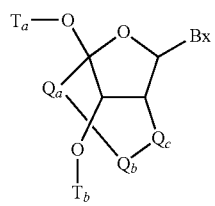

I wherein:

Bx is a nucleobase moiety;

-$Q_a$-$Q_b$-$Q_c$- is —$CH_2$—N($R_c$)—$CH_2$—, —C(=O)—N($R_c$)—$CH_2$—, —$CH_2$—O—N($R_c$)—, —$CH_2$—N($R_G$)—O—, or —N($R_c$)—O—$CH_2$;

$R_c$ is $C_1$-$C_{12}$ alkyl or an amino protecting group; and $T_a$ and $T_b$ are each, independently, H, a hydroxyl protecting group, a conjugate group, a reactive phosphorus group, a phosphorus moiety, or a covalent attachment to a support medium.

In certain embodiments, bicyclic nucleoside having Formula II:

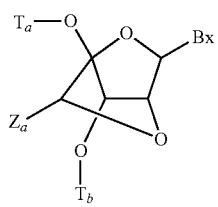

II wherein:

Bx is a nucleobase moiety;

$T_a$ and $T_b$ are each, independently, H, a hydroxyl protecting group, a conjugate group, a reactive phosphorus group, a phosphorus moiety, or a covalent attachment to a support medium;

$Z_a$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, substituted amide, thiol, or substituted thio.

In certain embodiments, each of the substituted groups is, independently, mono or poly substituted with substituent groups independently selected from halogen, oxo, hydroxyl, $OJ_c$, $NJ_cJ_d$, $SJ_c$, $N_3$, OC(=X)$J_c$, and $NJ_eC(=X)NJ_cJ_d$, wherein each $J_c$, $J_d$, and $J_e$ is, independently, H, $C_1$-$C_6$ alkyl, or substituted $C_1$-$C_6$ alkyl and X is O or $NJ_c$.

In certain embodiments, bicyclic nucleoside have Formula III:

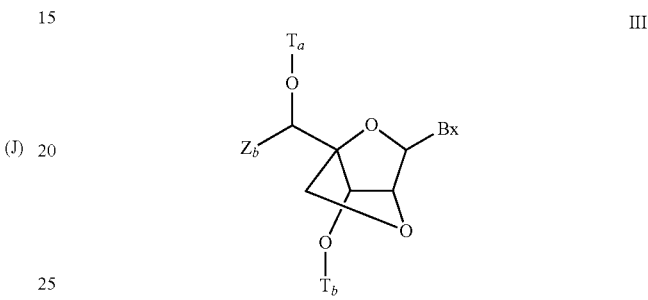

III wherein:

Bx is a nucleobase moiety;

$T_a$ and $T_b$ are each, independently, H, a hydroxyl protecting group, a conjugate group, a reactive phosphorus group, a phosphorus moiety, or a covalent attachment to a support medium;

$Z_b$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, or substituted acyl (C(=O)—).

In certain embodiments, bicyclic nucleoside having Formula IV:

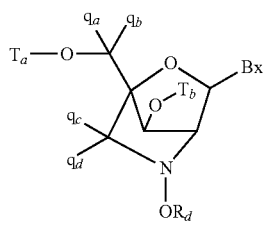

IV wherein:

Bx is a nucleobase moiety;

$T_a$ and $T_b$ are each, independently H, a hydroxyl protecting group, a conjugate group, a reactive phosphorus group, a phosphorus moiety, or a covalent attachment to a support medium;

$R_d$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl;

each $q_a$, $q_b$, $q_c$ and $q_d$ is, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl, or substituted $C_1$-$C_6$ aminoalkyl;

In certain embodiments, bicyclic nucleoside having Formula V:

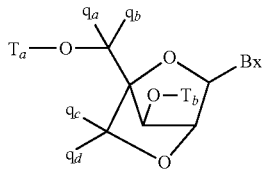

wherein:

Bx is a nucleobase moiety;

$T_a$ and $T_b$ are each, independently, H, a hydroxyl protecting group, a conjugate group, a reactive phosphorus group, a phosphorus moiety, or a covalent attachment to a support medium;

$q_a$, $q_b$, $q_e$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)—$NJ_jJ_k$, N(H)C(=NH)$NJ_jJ_k$, N(H)C(=O)$NJ_jJ_k$ or N(H)C(=S)$NJ_jJ_k$;

or $q_e$ and $q_f$ together are =C($q_g$)($q_h$);

$q_g$ and $q_h$ are each, independently, H, halogen, $C_1$-$C_{12}$ alkyl, or substituted $C_1$-$C_{12}$ alkyl.

In certain embodiments, bicyclic nucleoside having Formula VI:

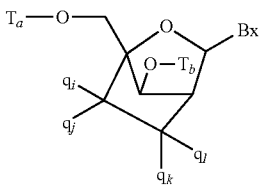

wherein:

Bx is a nucleobase moiety;

$T_a$ and $T_b$ are each, independently, H, a hydroxyl protecting group, a conjugate group, a reactive phosphorus group, a phosphorus moiety, or a covalent attachment to a support medium;

each $q_i$, $q_j$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$, or N(H)C(=S)$NJ_jJ_k$; and $q_i$ and $q_j$ or $q_l$ and $q_k$ together are =C($q_g$)($q_k$), wherein $q_g$ and $q_h$ are each, independently, H, halogen, $C_1$-$C_{12}$ alkyl, or substituted $C_1$-$C_{12}$ alkyl.

Additional bicyclic sugar moieties are known in the art, for example: Singh et al., *Chem. Commun.*, 1998, 4, 455-456; Koshkin et al., *Tetrahedron*, 1998, 54, 3607-3630; Wahlestedt et al., *Proc. Natl. Acad. Sci. U.S.A.*, 2000, 97, 5633-5638; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 129(26) 8362-8379 (Jul. 4, 2007); Elayadi et al., *Curr. Opinion Invens. Drugs*, 2001, 2, 558-561; Braasch et al., *Chem. Biol.*, 2001, 8, 1-7; Orum et al., *Curr. Opinion Mol. Ther.*, 2001, 3, 239-243; U.S. Pat. Nos. 7,053,207, 6,268,490, 6,770,748, 6,794,499, 7,034,133, 6,525,191, 6,670,461, and 7,399,845; WO 2004/106356, WO 1994/14226, WO 2005/021570, and WO 2007/134181; U.S. Patent Publication Nos. US2004/0171570, US2007/0287831, and US2008/0039618; U.S. patent Ser. Nos. 12/129,154, 60/989,574, 61/026,995, 61/026,998, 61/056,564, 61/086,231, 61/097,787, and 61/099,844; and PCT International Applications Nos. PCT/US2008/064591, PCT/US2008/066154, and PCT/US2008/068922.

In certain embodiments, bicyclic sugar moieties and nucleosides incorporating such bicyclic sugar moieties are further defined by isomeric configuration. For example, a nucleoside comprising a 4'-2' methylene-oxy bridge, may be in the α-L configuration or in the β-D configuration. Previously, α-L-methyleneoxy (4'-$CH_2$—O-2') bicyclic nucleosides have been incorporated into antisense oligonucleotides that showed antisense activity (Frieden et al., *Nucleic Acids Research*, 2003, 21, 6365-6372).

The synthesis and preparation of many bicyclic sugar moieties and bicyclic nucleosides has been described. For example, synthesis of methyleneoxy (4'-$CH_2$—O-2') BNA monomers adenine, cytosine, guanine, 5-methyl-cytosine, thymine, and uracil, along with their oligomerization, and nucleic acid recognition properties have been described (see, e.g., Koshkin et al., *Tetrahedron*, 1998, 54, 3607-3630). BNAs and preparation thereof are also described in WO 98/39352 and WO 99/14226. See also, Kumar et al., *Bioorg. Med. Chem. Lett.*, 1998, 8, 2219-2222; Wengel et al., WO 99/14226; Singh et al., *J. Org. Chem.*, 1998, 63, 10035-10039 (including synthesis of 2'-amino-BNA and 2'-amino- and 2'-methylamino-BNA').

In certain embodiments, substituted sugar moieties comprise one or more non-bridging sugar substituent and one or more bridging sugar substituent (e.g., 5'-substituted and 4'-2' bridged sugars). (see, PCT International Application WO 2007/134181, published on Nov. 22, 2007, wherein LNA is substituted with, for example, a 5'-methyl or a 5'-vinyl group).

In certain embodiments, modified sugar moieties are sugar surrogates. In certain such embodiments, the oxygen atom of the naturally occurring sugar is substituted, e.g., with a sulfur, carbon or nitrogen atom. In certain such embodiments, such modified sugar moiety also comprises bridging and/or non-bridging substituents as described above. For example, certain sugar surrogates comprise a 4'-sulfer atom and a substitution at the 2'-position (see, e.g., published U.S. Patent Application US2005/0130923, published on Jun. 16, 2005) and/or the 5' position. By way of additional example, carbocyclic bicyclic nucleosides having a 4'-2' bridge have been described (see, e.g., Freier et al., *Nucleic Acids Research*, 1997, 25(22), 4429-4443 and Albaek et al., *J. Org. Chem.*, 2006, 71, 7731-7740).

In certain embodiments, sugar surrogates comprise rings having other than 5-atoms. For example, in certain embodiments, a sugar surrogate comprises a six-membered tetrahydropyran. Such tetrahydropyrans may be further modified or substituted. Nucleosides comprising such modified tetrahydropyrans include, but are not limited to, hexitol nucleic acid (HNA), anitol nucleic acid (ANA), manitol nucleic acid (MNA) (see Leumann, C J. *Bioorg. & Med. Chem.* (2002) 10:841-854), fluoro HNA (F-HNA), and those compounds having Formula VII:

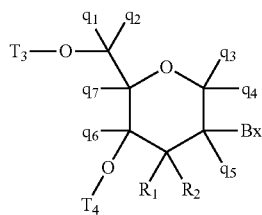

VII wherein independently for each of said at least one tetrahydropyran nucleoside analog of Formula X:

Bx is a nucleobase moiety;

$T_3$ and $T_4$ are each, independently, an internucleoside linking group linking the tetrahydropyran nucleoside analog to the antisense compound or one of $T_3$ and $T_4$ is an internucleoside linking group linking the tetrahydropyran nucleoside analog to the antisense compound and the other of $T_3$ and $T_4$ is H, a hydroxyl protecting group, a linked conjugate group, or a 5' or 3'-terminal group;

$q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and one of $R_1$ and $R_2$ is hydrogen and the other is selected from halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or $NJ_1$, and each $J_1$, $J_2$, and $J_3$ is, independently, H or $C_1$-$C_6$ alkyl.

In certain embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VII are provided wherein one of $R_1$ and $R_2$ is F. In certain embodiments, $R_1$ is fluoro and $R_2$ is H, $R_1$ is methoxy and $R_2$ is H, and $R_1$ is methoxyethoxy and $R_2$ is H.

Many other bicyclo and tricyclo sugar surrogate ring systems are also known in the art that can be used to modify nucleosides for incorporation into antisense compounds (see, e.g., review article: Leumann, J. C, *Bioorganic & Medicinal Chemistry*, 2002, 10, 841-854).

Combinations of modifications are also provided without limitation, such as 2'-F-5'-methyl substituted nucleosides (see PCT International Application WO 2008/101157 Published on Aug. 21, 2008 for other disclosed 5',2'-bis substituted nucleosides) and replacement of the ribosyl ring oxygen atom with S and further substitution at the 2'-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'-$CH_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., *J. Am. Chem. Soc.* 2007, 129(26), 8362-8379).

In certain embodiments, the present invention provides oligomeric compounds comprising recruiting nucleosides. In certain such embodiments, recruiting nucleosides comprise a modified sugar moiety. In certain contexts, any of the above described sugar modifications may be incorporated into a recruiting nucleoside.

In certain embodiments, the present invention provides oligomeric compounds comprising duplex stabilizing nucleosides. In certain such embodiments, duplex stabilizing nucleosides comprise a modified sugar moiety. In certain contexts, any of the above described sugar modifications may be incorporated into a stabilizing nucleoside.

Certain Nucleobases

In certain embodiments, nucleosides of the present invention comprise one or more unmodified nucleobases. In certain embodiments, nucleosides of the present invention comprise one or more modified nucleobases.

In certain embodiments, modified nucleobases are selected from: universal bases, hydrophobic bases, promiscuous bases, size-expanded bases, and fluorinated bases as defined herein. 5-substituted pyrimidines, 6-azapyrimidines and N-2, N-6 and O-6 substituted purines, including 2-aminopropyl-adenine, 5-propynyluracil; 5-propynylcytosine; 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein. Further modified nucleobases include tricyclic pyrimidines such as phenoxazine cytidine([5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, Kroschwitz, J. I., Ed., John Wiley & Sons, 1990, 858-859; those disclosed by Englisch et al., *Angewandte Chemie*, International Edition, 1991, 30, 613; and those disclosed by Sanghvi, Y. S., Chapter 15, *Antisense Research and Applications*, Crooke, S. T. and Lebleu, B., Eds., CRC Press, 1993, 273-288.

Representative United States patents that teach the preparation of certain of the above noted modified nucleobases as well as other modified nucleobases include without limitation, U.S. Pat. Nos. 3,687,808; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,681,941; 5,750,692; 5,763,588; 5,830,653 and 6,005,096, certain of which are commonly owned with the instant application, and each of which is herein incorporated by reference in its entirety.

Certain Internucleoside Linkages

In certain embodiments, the present invention provides oligomeric compounds comprising linked nucleosides. In such embodiments, nucleosides may be linked together using any internucleoside linkage. The two main classes of internucleoside linking groups are defined by the presence or absence of a phosphorus atom. Representative phosphorus containing internucleoside linkages include, but are not limited to, phosphodiesters (P═O), phosphotriesters, methylphosphonates, phosphoramidate, and phosphorothioates (P═S). Representative non-phosphorus containing internucleoside linking groups include, but are not limited to, methylenemethylimino (—$CH_2$—$N(CH_3)$—O—$CH_2$—), thiodiester (—O—C(O)—S—), thionocarbamate (—O—C(O)(NH)—S—); siloxane (—O—Si(H)$_2$—O—); and N,N'-dimethylhydrazine (—$CH_2$—$N(CH_3)$—$N(CH_3)$—). Modified linkages, compared to natural phosphodiester linkages, can be used to alter, typically increase, nuclease resistance of the oligomeric compound. In certain embodiments, internucleoside linkages having a chiral atom can be prepared a racemic mixture, as separate enantiomers. Representative chiral linkages include, but are not limited to, alkylphosphonates and phosphorothioates. Methods of preparation of phosphorous-containing and non-phosphorous-containing internucleoside linkages are well known to those skilled in the art.

The oligonucleotides described herein contain one or more asymmetric centers and thus give rise to enantiomers, diastereomers, and other stereoisomeric configurations that may be defined, in terms of absolute stereochemistry, as (R) or (S), α or β such as for sugar anomers, or as (D) or (L) such as for amino acids et al. Included in the antisense compounds provided herein are all such possible isomers, as well as their racemic and optically pure forms.

Neutral internucleoside linkages include without limitation, phosphotriesters, methylphosphonates, MMI (3'-$CH_2$—$N(CH_3)$—O-5'), amide-3 (3'-$CH_2$—C(═O)—N(H)-5'), amide-4 (3'-$CH_2$—N(H)—C(═O)-5'), formacetal (3'-O—$CH_2$—O-5'), and thioformacetal (3'-S—$CH_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and $CH_2$ component parts.

Certain Motifs

In certain embodiments, the present invention provides oligomeric compounds comprising oligonucleotides. In certain embodiments, such oligonucleotides comprise one or more chemical modification. In certain embodiments, chemically modified oligonucleotides comprise one or more modified sugar. In certain embodiments, chemically modified oligonucleotides comprise one or more modified nucleobase. In certain embodiments, chemically modified oligonucleotides comprise one or more modified internucleoside linkage. In certain embodiments, the chemically modifications (sugar modifications, nucleobase modifications, and/or linkage modifications) define a pattern or motif. In certain embodiments, the patterns of chemically modifications of sugar moieties, internucleoside linkages, and nucleobases are each independent of one another. Thus, an oligonucleotide may be described by its sugar modification motif, internucleoside linkage motif and/or nucleobase modification motif (as used herein, nucleobase modification motif describes the chemically modifications to the nucleobases independent of the sequence of nucleobases).

Certain Sugar Motifs

In certain embodiments, oligonucleotides comprise one or more type of modified sugar moieties and/or naturally occurring sugar moieties arranged along an oligonucleotide or region thereof in a defined pattern or sugar modification motif. In certain embodiments, the oligonucleotides of the present invention comprise or consist of a region that is uniformly sugar modified. In certain embodiments, the uniform sugar region comprises at least 5 contiguous nucleosides. In certain embodiments, the uniform sugar region comprises at least 7 contiguous nucleosides. In certain embodiments, the uniform sugar region comprises at least 9 contiguous nucleosides. In certain embodiments, the uniform sugar region comprises at least 10 contiguous nucleosides. In certain embodiments, the uniform sugar region comprises at least 11 contiguous nucleosides. In certain embodiments, the uniform sugar region comprises at least 12 contiguous nucleosides. In certain embodiments, the uniform sugar region comprises at least 13 contiguous nucleosides. In certain embodiments, the uniform sugar region comprises at least 14 contiguous nucleosides. In certain embodiments, the uniform sugar region comprises at least 15 contiguous nucleosides. In certain embodiments, the uniform sugar region comprises at least 16 contiguous nucleosides. In certain embodiments, the uniform sugar region comprises at least 18 contiguous nucleosides. In certain embodiments, the uniform sugar region comprises at least 20 contiguous nucleosides. In certain embodiments, the nucleosides of a uniform sugar region are recruiting nucleosides. In certain embodiments, the sugar moieties of the nucleosides of the uniform sugar region comprise a 2'-F. In certain embodiments, oligonucleotides consist of a uniform sugar region (i.e., comprise no nucleosides with different sugar modifications). In certain embodiments, oligonucleotides comprise one or more uniform sugar regions and one or more differently modified nucleosides.

In certain embodiments, the oligonucleotides comprise or consist of a region having a gapmer sugar modification motif, which comprises two external regions or "wings" and an internal region or "gap." The three regions of a gapmer motif (the 5'-wing, the gap, and the 3'-wing) form a contiguous sequence of nucleosides wherein the sugar moieties of the nucleosides of each of the wings are different from the sugar moieties of the nucleosides of the gap. Typically, the sugar moieties within each of the two wings are the same as one another and the sugar moieties within the gap are the same as one another. In certain embodiments, the sugar moieties of the two wings are the same as one another (symmetric gapmer). In certain embodiments, the sugar moieties in the 5'-wing are different from the sugar moieties in the 3'-wing (asymmetric gapmer).

In certain embodiments, the nucleosides of the 5'-wing and the nucleosides of the 3'-wing are sugar modified nucleosides. In certain embodiments, the nucleosides of the gap comprise 2'-F sugar moieties. In certain embodiments, the wings are each from 1 to 10 nucleosides in length. In certain embodiments, the wings are each from 1 to 5 nucleosides in length. In certain embodiments, the gap is from 5 to 25 nucleosides in length. In certain embodiments, the gap is from 8 to 18 nucleosides in length. In certain embodiments, gapmers may be described using the following formula:

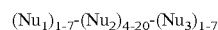

$(Nu_1)_{1-7}$-$(Nu_2)_{4-20}$-$(Nu_3)_{1-7}$ wherein $Nu_1$, $Nu_2$, and $Nu_3$ are nucleosides, wherein the sugar moieties of the $Nu_2$ nucleosides are different from the sugar moieties of the $Nu_1$ nucleosides and from the sugar moieties of the Nu$_3$ nucleosides and wherein the sugar moieties of the Nu$_1$ nucleosides and the Nu$_3$ nucleosides may be the same or different from one another. In certain embodiment, each Nu$_1$ is a duplex stabilizing nucleoside; each Nu$_3$ is a duplex stabilizing nucleoside; and each Nu$_2$ is a recruiting nucleoside. In certain embodiment, each Nu$_1$ is a 2'-MOE modified nucleoside; each Nu$_3$ is a 2'-MOE modified nucleoside; and each Nu$_2$ is a 2'-F modified nucleoside. In certain embodiments, gapmer oligonucleotides or regions can have any of the following, non-limiting list of numbers of nucleosides in the three regions (where the first number represents the number of nucleosides in the 5'-wing, the second number represents the number of nucleosides in the gap, and the third number represents the number of nucleosides in the 3'-wing): 1-18-1; 1-18-2; 2-18-1; 2-18-2; 1-17-1; 1-17-2; 2-17-1; 2-17-2; 3-17-2; 3-17-1; 2-17-2; 3-17-3; 1-16-1; 2-16-2; 3-16-3; 1-16-2; 2-16-1; 2-16-3; 3-16-2; 1-15-1; 2-15-2; 3-15-3; 4-15-4; 1-15-4; 4-15-1; 2-15-3; 1-14-1; 2-14-2; 3-14-3; 4-14-4; 1-14-2; 1-14-3; 2-14-3; 1-13-1; 2-13-2; 3; 13-3; 4-13-4; 1-13-2; 2-13- 3; 2-13-1; 4-13-2; 5-13-2; 5-13-4; 2-13-5; 1-12-1; 2-12-2; 3-12-3; 4-12-4; 5-12-5; 5-12-4; 4-12-5; 3-12-5; 5-12-3; 1-11-1; 2-11-2; 3-11-3; 4-11-4; 5-11-5; 6-11-6; 5-11-4; 4-11-5; 6-11-3; 3-11-5; 1-10-1; 2-10-2; 3-10-3; 4-10-4; 5-10-5; 6-10-6; 6-10-5; 5-10-6; 5-10-4; 4-10-5; 5-10-3; 3-10-5; 4-10-3; 3-10-4; 2-10-5; 5-10-2; 1-9-1; 2-9-2; 3-9-3; 4-9-4; 5-9-5; 6-9-6; 6-9-5; 5-9-6; 6-9-4; 4-9-6; 5-9-4; 4-9-5; 5-9-3; 3-9-5; 3-9-4; 4-9-3; 1-8-1-; 2-8-2; 3-8-3; 4-8-4; 5-8-5; 6-8-6; 6-8-5; 6-8-4; 6-8-3; 5-8-6; 4-8-6; 3-8- 6; 5-8-4; 5-8-3; 5-8-2; 4-8-2; 4-8-5; 4-8-3; 4-8-2; 1-7-1; 2-7-2; 3-7-3; 4-7-4; 5-7-5; 6-7-6; 1-6-1; 2-6-2; 3-6-3; 4-6-4; 5-6-5; and 6-6-6.

In certain embodiments, the sugar moieties of the nucleosides of one or both wings are modified sugar moieties. In certain such embodiments, the modified nucleosides of the 5'-wing comprise modified sugar moieties selected from any of the modified sugar moieties described herein. In certain such embodiments, the modified nucleosides of the 3'-wing comprise modified sugar moieties selected from any of the modified sugar moieties described herein. In certain embodiments, the nucleosides of the gap are 2'-F.

In certain embodiments, the sugar moieties of the wings are sugar moieties that adopt a 3'-endo or southern conformation. In certain such embodiments, the sugar moieties of the gap are sugar moieties that adopt a 2'-endo or northern conformation. In certain embodiments, the sugar moieties of both the 3'-wing and the 5'-wing comprise a 2'-MOE and the sugars of the nucleosides of the gap comprise a 2'-F.

In certain embodiments, one or both wing region comprises more than one type of sugar modification. For example, in certain embodiments, the 5'-wing region comprises two different types of sugar modifications, the gap region comprises nucleosides having a different type of sugar moities, and the 3' wing region comprises two different types of sugar modifications. Such a gapmer may be described using the earlier described convention, for example a (1-2)-14-(2-1) means that the 5'-wing comprises 3 nucleosides, wherein the 5' terminal nucleoside has a sugar modification of a first-type and the next two are of a different type, but the same as one another; the gap is 14 nucleosides in length; and the 3' wing comprises 3 nucleosides wherein the sugar moiety of the terminal nucleoside differs from that of the previous 2. Such gapmers are referred to herein as "mixed wing gapmers." Such mixed wing gapmers may have more than one type of sugar modification at the 5' wing (5'-mixed-wing gapmers); the 3' wing (3'-mixed wing gapmers); or both the 3'-wing and the 5'-wing (5'/3' mixed wing gapmers).

In certain embodiments, the oligonucleotides of the present invention comprise a region that is fully sugar modified, meaning that each nucleoside is a sugar modified nucleoside. The modifications of the nucleosides of a fully modified oligomeric compound may all be the same or one or more may be different from one another.

Certain Internucleoside Linkage Motifs

In certain embodiments, oligonucleotides comprise modified internucleoside linkages arranged along the oligonucleotide or region thereof in a defined pattern or modified internucleoside linkage motif. In certain embodiments, internucleoside linkages are arranged in a gapped motif, as described above for sugar modification motif. In such embodiments, the internucleoside linkages in each of two wing regions are different from the internucleoside linkages in the gap region. In certain embodiments the internucleoside linkages in the wings are phosphodiester and the internucleoside linkages in the gap are phosphorothioate. The sugar modification motif is independently selected, so such oligonucleotides having a gapped internucleotide linkage motif may or may not have a gapped sugar modification motif and if it does have a gapped sugar motif, the wing and gap lengths may or may not be the same.

In certain embodiments, oligonucleotides of the present invention comprise a region having an alternating internucleoside linkage motif. In certain embodiments, oligonucleotides of the present invention comprise a region of fully modified internucleoside linkages. In certain embodiments, oligonucleotides of the present invention comprise a region of uniformly modified internucleoside linkages. In certain such embodiments, the oligonucleotide comprises a region that is uniformly linked by phosphorothioate internucleoside linkages. In certain embodiments, the oligonucleotide is uniformly phosphorothioate. In certain embodiments, each internucleoside linkage of the oligonucleotide is selected from phosphodiester and phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least block of at least 6 consecutive phosphorothioate internucleoside linkages. In certain embodiments, the oligonucleotide comprises at least block of at least 8 consecutive phosphorothioate internucleoside linkages. In certain embodiments, the oligonucleotide comprises at least block of at least 10 consecutive phosphorothioate internucleoside linkages. In certain embodiments, the oligonucleotide comprises at least block of at least 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide.

Certain Nucleobase Modification Motifs

In certain embodiments, oligonucleotides comprise chemical modifications to nucleobases arranged along the oligonucleotide or region thereof in a defined pattern or nucleobases modification motif. In certain such embodiments, nucleobase modifications are arranged in a gapped motif. In certain embodiments, nucleobase modifications are arranged in an alternating motif. In certain embodiments, each nucleobase is modified (fully modified nucleobase motif). In certain embodiments, nucleobase modifications are uniform throughout an oligonucleotide. In certain embodiments, none of the nucleobases is chemically modified.

In certain embodiments, oligonucleotides comprise a block of modified nucleobases. In certain such embodiments, the block is at the 3'-end of the oligonucleotide. In certain embodiments the block is within 3 nucleotides of the 3'-end of the oligonucleotide. In certain such embodiments, the block is at the 5'-end of the oligonucleotide. In certain embodiments the block is within 3 nucleotides of the 5'-end of the oligonucleotide.

In certain embodiments, nucleobase modifications are a function of the natural base at a particular position of an oligonucleotide. For example, in certain embodiments each purine or each pyrimidine in an oligonucleotide is modified. In certain embodiments, each adenine is modified. In certain embodiments, each guanine is modified. In certain embodiments, each thymine is modified. In certain embodiments, each cytosine is modified. In certain embodiments, each uracil is modified.

In certain embodiments, some, all, or none of the cytosine moieties in an oligonucleotide are 5-methyl cytosine moieties. Herein, 5-methyl cytosine is not a "modified nucleobase." Accordingly, unless otherwise indicated, unmodified nucleobases include both cytosine residues having a 5-methyl and those lacking a 5 methyl. In certain embodiments, the methyl state of all or some cytosine nucleobases is specified.

Certain Overall Lengths

In certain embodiments, the present invention provides oligomeric compounds including oligonucleotides of any of a variety of ranges of lengths. In certain embodiments, the invention provides oligomeric compounds or oligonucleotides consisting of X to Y linked nucleosides, where X represents the fewest number of nucleosides in the range and Y represents the largest number of nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X≤Y. For example, in certain embodiments, the invention provides oligomeric compounds which comprise oligonucleotides consisting of 8 to 9, 8 to 10, 8 to 11, 8 to 12, 8 to 13, 8 to 14, 8 to 15, 8 to 16, 8 to 17, 8 to 18, 8 to 19, 8 to 20, 8 to 21, 8 to 22, 8 to 23, 8 to 24, 8 to 25, 8 to 26, 8 to 27, 8 to 28, 8 to 29, 8 to 30, 9 to 10, 9 to 11, 9 to 12, 9 to 13, 9 to 14, 9 to 15, 9 to 16, 9 to 17, 9 to 18, 9 to 19, 9 to 20, 9 to 21, 9 to 22, 9 to 23, 9 to 24, 9 to 25, 9 to 26, 9 to 27, 9 to 28, 9 to 29, 9 to 30, 10 to 11, 10 to 12, 10 to 13, 10 to 14, 10 to 15, 10 to 16, 10 to 17, 10 to 18, 10 to 19, 10 to 20, 10 to 21, 10 to 22, 10 to 23, 10 to 24, 10 to 25, 10 to 26, 10 to 27, 10 to 28, 10 to 29, 10 to 30, 11 to 12, 11 to 13, 11 to 14, 11 to 15, 11 to 16, 11 to 17, 11 to 18, 11 to 19, 11 to 20, 11 to 21, 11 to 22, 11 to 23, 11 to 24, 11 to 25, 11 to 26, 11 to 27, 11 to 28, 11 to 29, 11 to 30, 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides. In embodiments where the number of nucleosides of an oligomeric compound or oligonucleotide is limited, whether to a range or to a specific number, the oligomeric compound or oligonucleotide may, nonetheless further comprise additional other substituents. For example, an oligonucleotide comprising 8-30 nucleosides excludes oligonucleotides having 31 nucleosides, but, unless otherwise indicated, such an oligonucleotide may further comprise, for example one or more conjugates, terminal groups, or other substituents.

Certain Oligonucleotides

In certain embodiments, oligonucleotides of the present invention are characterized by their sugar motif, internucleoside linkage motif, nucleobase modification motif and overall length. In certain embodiments, such parameters are each independent of one another. Thus, each internucleoside linkage of an oligonucleotide having a gaped sugar motif may be modified or unmodified and may or may not follow the modification pattern of the sugar modifications. Thus, the internucleoside linkages within the wing regions of a sugar-gapmer may be the same or different from one another and may be the same or different from the internucleoside linkages of the gap region. Likewise, such sugar-gapmer oligonucleotides may comprise one or more modified nucleobase independent of the gapmer pattern of the sugar modifications. One of skill in the art will appreciate that such motifs may be combined to create or to describe a variety of oligonucleotides, such as those provided in the non-limiting table below.

| Overall Length | Sugar Motif | Internucleoside Linkage Motif | Nucleobase Mod. Motif |
|---|---|---|---|
| 20 | 5-10-5 gapmer w/2'MOE wings and 2'-F gap | uniform PS | uniform unmodified |
| 20 | 5-10-5 gapmer w/2'MOE wings and 2'-F gap | 2-14-2 gapmer: PO in wings and PS in gap | uniform unmodified |
| 20 | 5-10-5 gapmer w/BNA wings and 2'-F gap | uniform PS | uniform unmodified; all C's are 5-meC |

| Overall Length | Sugar Motif | Internucleoside Linkage Motif | Nucleobase Mod. Motif |
|---|---|---|---|
| 20 | 5-10-5 asymmetric gapmer w/2'MOE in 3'-wing; BNA in 5'-wing; and 2'-F gap | uniform PS | uniform unmodified; no Cs are 5-meC) |
| 18 | Uniform 2'-F | uniform PS | uniform unmodified; at least one nucleobase is a 5-meC |
| 16 | 2-12-2 gapmer w/BNA in each wing and 2'-F gap | uniform PS | uniform unmodified |
| 16 | 2-12-2 gapmer w/duplex stabilizing nuc. in each wing and recruiting nuc. gap | uniform PS | uniform unmodified |
| 14 | 2-10-2 gapmer w/2'-MOE in each wing and 2'-F gap | All PS or PO | uniform unmodified |
| 14 | 2-10-2 gapmer w/2'-BNA in each wing and 2'-F gap | uniform PS | uniform unmodified |
| 16 | 2-12-2 gapmer w/BNA in 5'-wing; 2'-MOE in 3'-wing; and 2'-F gap | uniform PS | uniform unmodified |
| 20 | 4-12-4 gapmer w/BNA in 5'-wing; mixed 2'-MOE and BNA in 3'-wing; and 2'-F gap | uniform PS | uniform unmodified |
| 22 | 5-12-5 gapmer w/BNA in 5'-wing; mixed 2'-MOE and BNA in 3'-wing; and 2'-F gap | uniform PS | uniform unmodified |
| 16 | (1-2)-10-(2-1) mixed wing gapmer: MOE-BNA-2'-F-BNA-MOE | uniform PS | unimform unmodified |

The above table is intended only to illustrate and not to limit the various combinations of the parameters of oligonucleotides of the present invention. Herein if a description of an oligonucleotide or oligomeric compound is silent with respect to one or more parameter, such parameter is not limited. Thus, an oligomeric compound described only as having a gapmer sugar motif without further description may have any length, internucleoside linkage motif, and nucleobase modification motif. Unless otherwise indicated, all chemical modifications are independent of nucleobase sequence.

In certain embodiments, the present invention provides oligomeric compounds comprising recruiting nucleosides. In certain such embodiments, recruiting nucleosides comprise a modified sugar moiety. In certain such embodiments, each modified sugar moiety is selected from: a 2'-F sugar moiety; tetrahydropyran sugar moiety (including, but not limited to, a F-substituted tetrahydropyran); a BNA (including, but not limited to, LNA, ENA, and cEt). In certain embodiments, antisense compounds of the present invention comprise a region of contiguous recruiting nucleosides. In certain embodiments, a region of recruiting nucleosides comprises at least 4 contiguous recruiting nucleosides. In certain embodiments, a region of recruiting nucleosides comprises at least 6 contiguous recruiting nucleosides. In certain embodiments, a region of recruiting nucleosides comprises at least 8 contiguous recruiting nucleosides. In certain embodiments, a region of recruiting nucleosides comprises at least 10 contiguous recruiting nucleosides. In certain embodiments, a region of recruiting nucleosides comprises at least 12 contiguous recruiting nucleosides. In certain embodiments, a region of recruiting nucleosides comprises at least 14 contiguous recruiting nucleosides. In certain embodiments, a region of recruiting nucleosides comprises at least 16 contiguous recruiting nucleosides. In certain embodiments, a region of recruiting nucleosides comprises at least 18 contiguous recruiting nucleosides. In certain embodiments, a region of recruiting nucleosides comprises at least 20 contiguous recruiting nucleosides. In certain embodiments, a region of recruiting nucleosides comprises at least 22 contiguous recruiting nucleosides. In certain embodiments, the recruiting nucleosides within a region all comprise the same modified sugar moiety.

In certain embodiments, oligonucleotides of the present invention comprise one or more duplex stabilizing nucleosides, which comprises a modified sugar moiety making them more stable than naturally occurring nucleosides. In certain embodiments, duplex stabilizing nucleosides comprise a substituted sugar moiety. In certain embodiments, duplex stabilizing nucleosides comprise a sugar surrogate. In certain embodiments, duplex stabilizing nucleosides comprise 2'-MOE sugar moieties. In certain embodiments, the invention provides a region of 1-5 duplex stabilizing nucleosides at one or both ends of an oligonucleotide.

In certain embodiments, antisense compounds of the present invention comprise a gapmer sugar motif, wherein the nucleosides of the gap are recruiting nucleosides and the nucleosides of the wings are duplex stabilizing nucleosides. In certain such embodiments, antisense compounds comprise the sugar motif: 2'-MOE:2'-F:2'-MOE. In certain such embodiments, antisense compounds comprise the sugar motif: 2'-MOE:BNA:2'-MOE. In certain such embodiments, antisense compounds comprise the sugar motif: 2'-MOE:cEt:2'-MOE.

Certain Conjugate Groups

In certain embodiments, oligomeric compounds are modified by attachment of one or more conjugate groups. In general, conjugate groups modify one or more properties of the attached oligomeric compound including but not limited to pharmacodynamics, pharmacokinetics, stability, binding, absorption, cellular distribution, cellular uptake, charge and clearance. Conjugate groups are routinely used in the chemical arts and are linked directly or via an optional conjugate linking moiety or conjugate linking group to a parent compound such as an oligomeric compound, such as an oligonucleotide. Conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes. Certain conjugate groups have been described previously, for example: cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., do-decan-diol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937).

In certain embodiments, a conjugate group comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indo-methicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130.

In certain embodiments, conjugate groups are directly attached to oligonucleotides in oligomeric compounds. In certain embodiments, conjugate groups are attached to oligonucleotides by a conjugate linking group. In certain such embodiments, conjugate linking groups, including, but not limited to, bifunctional linking moieties such as those known in the art are amenable to the compounds provided herein. Conjugate linking groups are useful for attachment of conjugate groups, such as chemical stabilizing groups, functional groups, reporter groups and other groups to selective sites in a parent compound such as for example an oligomeric compound. In general a bifunctional linking moiety comprises a hydrocarbyl moiety having two functional groups. One of the functional groups is selected to bind to a parent molecule or compound of interest and the other is selected to bind essentially any selected group such as chemical functional group or a conjugate group. In some embodiments, the conjugate linker comprises a chain structure or an oligomer of repeating units such as ethylene glycol or amino acid units. Examples of functional groups that are routinely used in a bifunctional linking moiety include, but are not limited to, electrophiles for reacting with nucleophilic groups and nucleophiles for reacting with electrophilic groups. In some embodiments, bifunctional linking moieties include amino, hydroxyl, carboxylic acid, thiol, unsaturations (e.g., double or triple bonds), and the like.

Some nonlimiting examples of conjugate linking moieties include pyrrolidine, 8-amino-3,6-dioxaoctanoic acid (ADO), succinimidyl 4-(N-maleimidomethyl)cyclohexane-1-carboxylate (SMCC) and 6-aminohexanoic acid (AHEX or AHA). Other linking groups include, but are not limited to, substituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

Conjugate groups may be attached to either or both ends of an oligonucleotide (terminal conjugate groups) and/or at any internal position.

In certain embodiments, conjugate groups are at the 3'-end of an oligonucleotide of an oligomeric compound. In certain embodiments, conjugate groups are near the 3'-end. In certain embodiments, conjugates are attached at the 3' end of an oligomeric compound, but before one or more terminal group nucleosides. In certain embodiments, conjugate groups are placed within a terminal group.

In certain embodiments, the present invention provides oligomeric compounds. In certain embodiments, oligomeric compounds comprise an oligonucleotide. In certain embodiments, an oligomeric compound comprises an oligonucleotide and one or more conjugate and/or terminal groups. Such conjugate and/or terminal groups may be added to oligonucleotides having any of the chemical motifs discussed above. Thus, for example, an oligomeric compound comprising an oligonucleotide having region of alternating nucleosides may comprise a terminal group.

Antisense Compounds

In certain embodiments, oligomeric compounds of the present invention are antisense compounds. Such antisense compounds are capable of hybridizing to a target nucleic acid, resulting in at least one antisense activity. In certain embodiments, antisense compounds specifically hybridize to one or more target nucleic acid. In certain embodiments, a specifically hybridizing antisense compound has a nucleobase sequence comprising a region having sufficient complementarity to a target nucleic acid to allow hybridization and result in antisense activity and insufficient complementarity to any non-target so as to avoid non-specific hybridization to any non-target nucleic acid sequences under conditions in which specific hybridization is desired (e.g., under physiological conditions for in vivo or therapeutic uses, and under conditions in which assays are performed in the case of in vitro assays).

In certain embodiments, the present invention provides antisense compounds comprising oligonucleotides that are fully complementary to the target nucleic acid over the entire length of the oligonucleotide. In certain embodiments, oligonucleotides are 99% complementary to the target nucleic acid. In certain embodiments, oligonucleotides are 95% complementary to the target nucleic acid. In certain embodiments, such oligonucleotides are 90% complementary to the target nucleic acid.

In certain embodiments, such oligonucleotides are 85% complementary to the target nucleic acid. In certain embodiments, such oligonucleotides are 80% complementary to the target nucleic acid. In certain embodiments, an antisense compound comprises a region that is fully complementary to a target nucleic acid and is at least 80% complementary to the target nucleic acid over the entire length of the oligonucleotide. In certain such embodiments, the region of full complemenarity is from 6 to 14 nucleobases in length.

Certain Antisense Activities and Mechanisms

In certain antisense activities, hybridization of an antisense compound results in recruitment of a protein that cleaves of the target nucleic acid. For example, certain antisense compounds result in RNase H mediated cleavage of target nucleic acid. RNase H is a cellular endonuclease that cleaves the RNA strand of an RNA:DNA duplex. The "DNA" in such an RNA:DNA duplex, need not be unmodified DNA. In certain embodiments, the invention provides antisense compounds that are sufficiently "DNA-like" to elicit RNase H activity. Such DNA-like antisense compounds include, but are not limited to gapmers having unmodified deoxyfuronose sugar moieties in the nucleosides of the gap and modified sugar moieties in the nucleosides of the wings. Another example of antisense mechanisms that may result in cleavage of a target nucleic acid are RNAi mechanisms, which utilize the RISC pathway. Antisense compounds that elicit cleavage at least in part via RNAi mechanisms include short-interfering RNAs (siRNA), which are typically double-stranded, and single-stranded RNAi compounds (ssRNAi). Such antisense compounds typically comprise one or more RNA nucleosides or modified nucleosides that are RNA-like.

In certain embodiments, the present invention provides antisense oligonucleotides that hybridize to a target nucleic acid resulting in a duplex that recruits one or more protein that does not cleave the target nucleic acid (a non-cleaving protein). Accordingly, in such embodiments, the recruited protein is not RNase H or Ago2 (the nuclease in the RISC pathway). In certain embodiments, the antisense activity includes reduced expression of a protein encoded by the target nucleic acid, without relying in recruitment of a cleaving protein to the target nucleic acid. In certain embodiments, the antisense activity is altered splicing of the target nucleic acid. In certain embodiments, the antisense activity is altered localization of the target nucleic acid. In certain embodiments, the antisense activity is disruption of target RNA function.

Certain antisense mechanisms typically do not promote immediate enzyme mediated cleavage of the target nucleic acid, but nonetheless disrupt or alter its function or activity. For example, microRNA mimics involve certain components of the RISC pathway, but typically result in sequestration, rather than immediate cleavage of the target nucleic acid. Certain antisense compounds exert antisense activity by occupancy (i.e., presence of the antisense compound hybridized to the target nucleic acid results in a change in the function of the target nucleic acid and/or in the way the target nucleic acid interacts with another molecule). For example, in certain embodiments, antisense compounds hybridize to a pre-mRNA and alter processing of the pre-mRNA. For example, in certain embodiments, the antisense compound modulates polyadenylation and/or addition of the 5'-cap. In certain such embodiments, the resulting mRNA with altered or absent polyadenylation or 5-cap may be less stable than the non-modulated form. Thus, the antisense activity may ultimately result in the generation of a mature mRNA that is degraded more quickly than one in which such functions has not been altered. In certain embodiments, antisense compounds of the present invention are not microRNA mimics. In certain embodiments, the non-cleaving protein recruited by an antisense oligonucleotide of the present invention is not a member of the RISC pathway.

In certain embodiments, an antisense compound alters splicing of the pre-mRNA, resulting in a differently spliced mature mRNA. Modulation of splicing may result in a change in the inclusion or exclusion of a portion of pre-mRNA (intron, exon, alternate intron, or alternate exon) in the mature mRNA compared to that of a mature mRNA in the absence of the antisense compound. Such splice-altered mature mRNA may have different stability characteristics. Thus, the splice-altered mRNA may degrade more or less quickly or be translated more or less efficiently resulting in a corresponding increase or decrease in the protein expressed from the mature mRNA, even if the identity of the translated protein is unchanged or essentially unchanged (e.g., a "silent" difference where the two mature mRNAs encode the same or similar protein but have different properties). In certain embodiments, a splice-altered mature mRNA may encode a different protein than the unaltered mRNA. In certain embodiments, an antisense compound alters the ratio of splice variants of a protein product, wherein both splice variants are present in the absence of the antisense compound, but at different amounts. In certain embodiments, an antisense compound alters splicing ultimately resulting in a protein product that is not present in the absence of the antisense compound.

Antisense activities may be observed directly or indirectly. In certain embodiments, observation or detection of an antisense activity involves observation or detection of a change in an amount of a target nucleic acid or protein encoded by such target nucleic acid; a change in the ratio of splice variants of a nucleic acid or protein; and/or a phenotypic change in a cell or animal.

Recruitment of Non-Cleaving Proteins

Certain aspects of the present invention flow from the discovery that certain oligonucleotide/target nucleic acid duplexes recruit certain proteins. Further, the identity of such recruited proteins that bind or interact with such an oligonucleotide/target nucleic acid duplex can be determined. In certain instances, such recruited proteins differ depending on chemical modifications and/or motifs of the oligonucleotide. In certain embodiments, one may select a target nucleic acid; a target region within the target nucleic acid; and a chemical modification motif to prepare an oligonucleotide to recruit one or more desired protein to a target region of the target nucleic acid. In certain embodiments, the selections are driven by the desired outcome. For example, certain recruitable proteins are associated with modulation of splicing. In certain embodiments, the invention provides a method of modulating splicing of a target pre-mRNA comprising contacting a cell with an oligonucleotide complementary to the pre-mRNA at a region at or near where the modulation is desired and comprising chemical modifications that recruit one or more protein to the oligonucleotide/target pre-mRNA duplex, wherein the one or more protein modulates pre-mRNA splicing. In certain such embodiments, one or more of the recruited proteins actively modulates splicing by participating in the splicing reaction or by interacting with other splicing factors. In certain embodiments, one or more of the recruited proteins does not directly mediate the desired outcome, but its presence at the oligonucleotide/target nucleic acid duplex prevents a reaction that would otherwise occur. For example, certain recruited proteins may have little or no direct activity once recruited to the duplex, however, they prevent an interaction that would otherwise occur. For example, in certain instances, in the absence of an antisense oligonucleotide and subsequent binding of a recruited protein, a splice factor would bind to the target pre-mRNA at or near the target site and would effect a splicing reaction. In such instances, modulation of splicing may be achieved by an ASO recruiting a protein to the target site and subsequent blocking of the splicing factor by the mere presence of the recruited protein, though it has no direct activity.

Certain different proteins are recruited to nucleic acids with a variety of results, depending on the particular protein. For example, recruitment of certain proteins to a nucleic acid results in that nucleic acid being localized within a cell: for example a particular organelle or sub-organelle, or distinct region of a cell (e.g., axon of a neuron). In certain embodiments, an oligonucleotide comprising certain chemical modifications may be used to recruit such proteins to a target nucleic acid to direct localization of the target nucleic acid within a cell.

Certain proteins effect polyadneylation of a pre-mRNA. Such proteins may be recruited to a nucleic acid target to prevent or illicit polyadenlyation of the target nucleic acid. Certain proteins effect addition of a 5'-cap to a pre-mRNA. Such proteins may be recruited to a nucleic acid target to prevent or illicit addition of a 5' cap to the target nucleic acid.

Certain proteins effect translation of an mRNA. Such proteins may be recruited to a nucleic acid target to modulate translation of the target nucleic acid.

Certain proteins, when bound to a target nucleic acid direct splicing of the target nucleic acid. Thus, oligonucleotides comprising chemical modifications that recruit such proteins may be used to direct splicing at or near a target site on a target nucleic acid. Certain proteins when bound to a nucleic acid modulate the function of that nucleic acid. Thus, oligonucleotides comprising chemical modifications that recruit such proteins to a target nucleic acid may be used to modulate the function of the target nucleic acid. Certain proteins, when bound to a target nucleic acid have little or no effect. Such proteins may be recruited to a target nucleic acid to prevent an interaction that would otherwise occur.

In certain of such embodiments, the antisense oligonucleotide recruits to the target nucleic acid a protein that would not ordinarily interact with that nucleic acid. In certain of such embodiments, the antisense oligonucleotide recruits to the target nucleic acid a protein that would not ordinarily interact with the target region of that nucleic acid. In certain of such embodiments, the antisense oligonucleotide increases recruitment to the target nucleic acid of a protein that would ordinarily interact with that nucleic acid at a lower level or amount.

In certain embodiments, the present invention provides methods of inducing exon skipping comprising contacting a cell with an antisense compound complementary to a pre-mRNA at or near the exon to be skipped, wherein the antisense compound comprises sufficient recruiting nucleosides to recruit a non-cleaving protein to the pre-mRNA/antisense compound duplex to alter splicing of the pre-mRNA. In certain embodiments, the non-cleaving protein is a splicing factor. In certain embodiments, the non-cleaving protein is not a splicing factor. In certain such embodiments, recruitment of the non-cleaving protein that is not a splicing factor prevents binding of a splicing factor. In certain embodiments, the non-cleaving protein is selected from ILF2 and ILF3.

In certain embodiments, the invention provides methods for identifying proteins that may be recruited to certain target nucleic acid/oligonucleotide duplexes. For example, the methods described in the present examples may be exploited using oligonucleotides having any chemical modification or motif to identify one or more protein that is recruited to a duplex comprising such oligonucleotide and a target nucleic acid. The identity of such recruited protein will suggest potential uses and indications. For example, the present invention demonstrates the oligonucleotides comprising region of contiguous 2'-F modified nucleosides hybridize to a target RNA to form a duplex that recruits ILF-2&3. Since ILF-2&3 has previously been shown to modulate transcription reactions, including those associated with T-cell expression, one may manipulate such reactions and/or direct them to a desired target nucleic acid using such oligonucleotides comprising a region of 2'-F modified nucleosides. Further, in instances where ILF-2&3 does not support splicing reactions, it is appreciated that oligonucleotides having such contiguous region of 2'F modified nucleosides may be used to disrupt splicing by recruiting it to a target site where interaction of a splice factor is required for normal splicing. In certain embodiments, the presence of a recruited protein blocks interactions more completely or over a longer region of a target nucleic acid compared to the effect of binding an oligonucleotide that does not recruit a protein. The presence of the ILF-2&3 will, in certain instances, displace the required splice factor, disrupting normal splicing. Depending on whether the splice factor is a splice enhancer or a splice suppressor, splicing may be modulated up or down. In certain embodiments, the target site is a splice enhancer and the antisense compound recruits ILF2&3, preventing normal splice factors from interacting to enhance splicing and normal splicing is thereby inhibited, resulting in skipping of an exon that would otherwise be included.

In certain embodiments the invention provides methods for functionalizing a protein of interest. For example, in certain embodiments, the invention provides methods of screening duplexes for their ability to recruit a protein of interest, wherein the duplex comprises a naturally occurring nucleic acid and a chemically modified oligonucleotide. One may test several oligonucleotides, each having a different motif of chemical modifications. Once a duplex capable of recruiting the protein of interest is identified, antisense oligonucleotides comprising that motif and having a nucleobase sequence complementary to a particular nucleic acid target or target site may be prepared. Such antisense oligonucleotides may be used to recruit the protein of interest to the various target nucleic acids or sites. In such embodiments, the effect on the target nucleic acid is observed to determine the function of the protein of interest.

Modulation of Splicing

Certain antisense compounds form a duplex with a target pre-mRNA to modulate splicing. Certain such antisense compounds induce exclusion of an exon. Such induced exclusion of an exon has potential therapeutic uses. For example a number of conditions result from undesired inclusion of one or more exon. In certain embodiments, exclusion of an exon is used for therapeutic advantage. For example, Duchenne muscular dystrophy is characterized by a mutation that causes a frame shift resulting in a protein having little or no activity. In certain embodiments, if the exon comprising the mutation is skipped entirely, the resulting protein, though missing a domain corresponding to the skipped exon, is more functional because the frame shift is corrected. In certain embodiments, the exon skipping antisense oligonucleotides describe herein may be used to treat Duchenne muscular dystrophy. In certain instances a protein lacking one or more exon is inactive. In certain embodiments, it is therapeutically desired to inactivate a particular protein (e.g., its over-expression is causing disease). In such embodiments, inducing skipping of an exon required for protein function may have therapeutic value.

In certain embodiments, antisense compounds having motifs described herein may modulate splicing without recruiting a non-cleaving protein to the target nucleic acid. In certain embodiments, the invention provides antisense compounds that promote exon skipping regardless of the mechanism. In certain such embodiments, the antisense compound targets a region within an intron. In certain such embodiments, the antisense compound targets a region within an exon. In certain such embodiments, the antisense compound targets an intron/exon junction.

Certain Target Nucleic Acids

In certain embodiments, antisense compounds comprise or consist of an oligonucleotide comprising a region that is complementary to a target nucleic acid. In certain embodiments, the target nucleic acid is an endogenous RNA molecule. In certain embodiments, the target nucleic acid is a non-coding RNA. In certain such embodiments, the target non-coding RNA is selected from: a long-non-coding RNA, a short non-coding RNA, an intronic RNA molecule, a snoRNA, a scaRNA, a microRNA (including pre-microRNA and mature microRNA), a ribosomal RNA, and promoter directed RNA. In certain embodiments, the target nucleic acid encodes a protein. In certain such embodiments, the target nucleic acid is selected from: an mRNA and a pre-mRNA, including intronic, exonic and untranslated regions. In certain embodiments, oligomeric compounds are at least partially complementary to more than one target nucleic acid. For example, antisense compounds of the present invention may mimic microRNAs, which typically bind to multiple targets.

In certain embodiments, the target nucleic acid is a nucleic acid other than a mature mRNA. In certain embodiments, the target nucleic acid is a nucleic acid other than a mature mRNA or a microRNA. In certain embodiments, the target nucleic acid is a non-coding RNA other than a microRNA. In certain embodiments, the target nucleic acid is a non-coding RNA other than a microRNA or an intronic region of a pre-mRNA. In certain embodiments, the target nucleic acid is a long non-coding RNA. In certain embodiments, the target RNA is an mRNA. In certain embodiments, the target nucleic acid is a pre-mRNA. In certain such embodiments, the target region is entirely within an intron. In certain embodiments, the target region spans an intron/exon junction. In certain embodiments, the target region is at least 50% within an intron. In certain embodiments, the target nucleic acid is selected from among non-coding RNA, including exonic regions of pre-mRNA. In certain embodiments, the target nucleic acid is a ribosomal RNA (rRNA). In certain embodiments, the target nucleic acid is a non-coding RNA associated with splicing of other pre-mRNAs. In certain embodiments, the target nucleic acid is a nuclear-retained non-coding RNA.

In certain embodiments, a target nucleic acid is a pre-mRNA. In certain embodiments, a target nucleic acid is a pre-mRNA encoding SMN2. In certain embodiments, a target nucleic acid is a pre-mRNA encoding a protein other than SMN2. In certain embodiments, the invention provides methods of inducing skipping of an exon of a pre-mRNA other than SMN2 in a cell comprising contacting the cell with an antisense compound comprising at least 8 contiguous 2'-F modified nucleosides. In certain embodiments, the antisense compound is complementary to a region of the pre-mRNA entirely within the intron immediately 3' of the exon, the skipping of which is induced. In certain such embodiments, the antisense compound is complementary to a region of the pre-mRNA entirely within the intron immediately 5' of the exon, the skipping of which is induced. In certain such embodiments, the antisense compound is complementary to a region of the pre-mRNA entirely within the exon, the skipping of which is induced. In certain embodiments, the antisense compound is complementary to a region of the pre-mRNA spanning the intron/exon junction at the 3' end of the exon the skipping of which is induced. In certain embodiments, the antisense compound is complementary to a region of the pre-mRNA spanning the intron/exon junction at the 5' end of the exon the skipping of which is induced.

In certain embodiments, antisense compounds recruit proteins that once bound to the antisense compound/target nucleic acid duplex disrupt U1 snRNP. In certain such embodiments, the target site is at or near the 5' splice site of an intron. In certain such embodiments, the recruited protein prevents U1 snRNP from splicing normally and the exon is skipped.

In certain embodiments, the target nucleic acid is a non-coding RNA that modulates an object nucleic acid. In certain embodiments, the object nucleic acid is an object RNA. In certain such embodiments, the target nucleic acid modulates splicing of an object pre-mRNA. In certain embodiments, an antisense compound of the present invention hybridizes to a target non-coding RNA to recruit a protein which in turn disrupts the normal interaction between the target non-coding RNA and an object RNA. In certain such embodiments, such disruption results in alternative splicing of an object pre-mRNA.

Certain Pharmaceutical Compositions

In certain embodiments, the present invention provides pharmaceutical compositions comprising one or more antisense compound. In certain embodiments, such pharmaceutical composition comprises a a suitable pharmaceutically acceptable diluent or carrier. In certain embodiments, a pharmaceutical composition comprises a sterile saline solution and one or more antisense compound. In certain embodiments, such pharmaceutical composition consists of a sterile saline solution and one or more antisense compound. In certain embodiments, the sterile saline is pharmaceutical grade saline. In certain embodiments, a pharmaceutical composition comprises one or more antisense compound and sterile water. In certain embodiments, a pharmaceutical composition consists of one or more antisense compound and sterile water. In certain embodiments, the sterile saline is pharmaceutical grade water. In certain embodiments, a pharmaceutical composition comprises one or more antisense compound and phosphate-buffered saline (PBS). In certain embodiments, a pharmaceutical composition consists of one or more antisense compound and sterile phosphate-buffered saline (PBS). In certain embodiments, the sterile saline is pharmaceutical grade PBS.

In certain embodiments, antisense compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

Pharmaceutical compositions comprising antisense compounds encompass any pharmaceutically acceptable salts, esters, or salts of such esters. In certain embodiments, pharmaceutical compositions comprising antisense compounds comprise one or more oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an oligomeric compound which are cleaved by endogenous nucleases within the body, to form the active antisense oligomeric compound.

Lipid moieties have been used in nucleic acid therapies in a variety of methods. In certain such methods, the nucleic acid is introduced into preformed liposomes or lipoplexes made of mixtures of cationic lipids and neutral lipids. In certain methods, DNA complexes with mono- or polycationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, INTRALIPID is used to prepare a pharmaceutical composition comprising an oligonucleotide. Intralipid is fat emulsion prepared for intravenous administration. It is made up of 10% soybean oil, 1.2% egg yolk phospholipids, 2.25% glycerin, and water for injection. In addition, sodium hydroxide has been added to adjust the pH so that the final product pH range is 6 to 8.9.

In certain embodiments, a pharmaceutical composition provided herein comprise a polyamine compound or a lipid moiety complexed with a nucleic acid. In certain embodiments, such preparations comprise one or more compounds each individually having a structure defined by formula (I) or a pharmaceutically acceptable salt thereof,

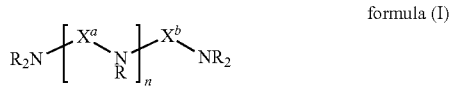

formula (I)

wherein each $X^a$ and $X^b$, for each occurrence, is independently $C_{1-6}$ alkylene; n is 0, 1, 2, 3, 4, or 5; each R is independently H, wherein at least n+2 of the R moieties in at least about 80% of the molecules of the compound of formula (I) in the preparation are not H; m is 1, 2, 3 or 4; Y is O, $NR^2$, or S; $R^1$ is alkyl, alkenyl, or alkynyl; each of which is optionally substituted with one or more substituents; and $R^2$ is H, alkyl, alkenyl, or alkynyl; each of which is optionally substituted each of which is optionally substituted with one or more substituents; provided that, if n=0, then at least n+3 of the R moieties are not H. Such preparations are described in PCT publication WO/2008/042973, which is herein incorporated by reference in its entirety for the disclosure of lipid preparations. Certain additional preparations are described in Akinc et al., *Nature Biotechnology* 26, 561-569 (1 May 2008), which is herein incorporated by reference in its entirety for the disclosure of lipid preparations.

In certain embodiments, pharmaceutical compositions provided herein comprise one or more modified oligonucleotides and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, a pharmaceutical composition provided herein comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition provided herein comprises one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, a pharmaceutical composition provided herein comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition provided herein is prepared for oral administration. In certain embodiments, pharmaceutical compositions are prepared for buccal administration.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

In certain embodiments, a pharmaceutical composition is prepared for transmucosal administration. In certain of such embodiments penetrants appropriate to the barrier to be permeated are used in the formulation. Such penetrants are generally known in the art.

In certain embodiments, a pharmaceutical composition provided herein comprises an oligonucleotide in a therapeutically effective amount. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, one or more modified oligonucleotide provided herein is formulated as a prodrug. In certain embodiments, upon in vivo administration, a prodrug is chemically converted to the biologically, pharmaceutically or therapeutically more active form of an oligonucleotide. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, prodrugs are less water soluble than the corresponding active form. In certain instances, such prodrugs possess superior transmittal across cell membranes, where water solubility is detrimental to mobility. In certain embodiments, a prodrug is an ester. In certain such embodiments, the ester is metabolically hydrolyzed to carboxylic acid upon administration. In certain instances the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form.

In certain embodiments, the present invention provides compositions and methods for reducing the amount or activity of a target nucleic acid in a cell. In certain embodiments, the cell is in an animal. In certain embodiments, the animal is a mammal. In certain embodiments, the animal is a rodent. In certain embodiments, the animal is a primate. In certain embodiments, the animal is a non-human primate. In certain embodiments, the animal is a human.

In certain embodiments, the present invention provides methods of administering a pharmaceutical composition comprising an oligomeric compound of the present invention to an animal. Suitable administration routes include, but are not limited to, oral, rectal, transmucosal, intestinal, enteral, topical, suppository, through inhalation, intrathecal, intracerebroventricular, intraperitoneal, intranasal, intraocular, intratumoral, and parenteral (e.g., intravenous, intramuscular, intramedullary, and subcutaneous). In certain embodiments, pharmaceutical intrathecals are administered to achieve local rather than systemic exposures. For example, pharmaceutical compositions may be injected directly in the area of desired effect (e.g., into the liver).

Nonlimiting Disclosure and Incorporation by Reference

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine(methylated uracil) for natural uracil of RNA).

Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified bases, such as "AT$^{me}$CGAUCG," wherein $^{me}$C indicates a cytosine base comprising a methyl group at the 5-position.

Likewise, one of skill will appreciate that in certain circumstances using the conventions described herein, the same compound may be described in more than one way. For example, an antisense oligomeric compound having two non-hybridizing 3'-terminal 2'-MOE modified nucleosides, but otherwise fully complementary to a target nucleic acid may be described as an oligonucleotide comprising a region of 2'-MOE-modified nucleosides, wherein the oligonucleotide is less than 100% complementary to its target. Or that same compound may be described as an oligomeric compound comprising: (1) an oligonucleotide that is 100% complementary to its nucleic acid target and (2) a terminal group wherein the terminal group comprises two 2'-MOE modified terminal-group nucleosides. Such descriptions are not intended to be exclusive of one another or to exclude overlapping subject matter.

EXAMPLES

Example 1

Antisense Oligonucleotides Targeting Human SMN

Antisense oligonucleotides complementary to human SMN2 were synthesized using standard techniques previously described.

| ISI No. | Sequence | Target region | TSS ID | SEQ ID NO |
|---|---|---|---|---|
| 444477 | $A_eT_eA_eG_eA_eT_eA_eT_eA_eG_eA_eT_eA_eG_e{}^{Me}C_eT_eA_eT_e$ | 26943-26960 | I061216 | 1 |
| 447440 | $A_eT_eA_dG_dA_dT_dA_dT_dA_dG_dA_dT_dA_dG_dC_dT_eA_eT_e$ | 26943-26960 | I061216 | 2 |

-continued

| ISI No. | Sequence | Target region | TSS ID | SEQ ID NO |
|---|---|---|---|---|
| 396443 | $T_e{}^{Me}C_eA_e{}^{Me}C_eT_eT_eT_e{}^{Me}C_eA_eT_eA_eA_eT_eG_e{}^{Me}C_eT_eG_eG_e$ | 27062-27079 | I061216 | 3 |
| 413147 | $T_e{}^{Me}C_eA_fC_fU_fU_fU_fC_fA_fU_fA_fA_fU_fG_fC_fU_fG_eG_e$ | 27062-27079 | I061216 | 4 |

Subscript "e" indicates that the preceding nucleoside comprises a 2'-MOE sugar moiety.
Subscript "f" indicates that the preceding nucleoside comprises a 2'-F sugar moiety.
Superscript "Me" indicates a 5-methyl group on the pyrimidine base of the preceding nucleoside.
All ASOs in the above table had phosphorothioate linkages (PS) throughout.

Example 2

Effect of ASOs on Splicing of SMN 1 and SMN2

The antisense oligonucleotides (ASOs) from Example 1 were tested for their ability to modulate splicing of SMN1 and SMN2. HeLa cells were transfected with 30 nM of one of the ASOs with Cytofectin or were left untreated as a control for 24 hours. RNA was isolated from the cells and analyzed by RT-PCR, using standard techniques. After PCR, samples were digested by DdeI, to distinguish SMN2 from SMN1 as previously described (e.g., Hua, et al., The American Journal of Human Genetics, 82, 1-15, April 2008). The digested products were resolved on an agarose gel and visualized by ethidium bromide staining (provided as FIG. 1).

Control cells show the native splicing pattern: SMN1 is spliced to mostly include exon 7; and SMN2 is alternatively spliced resulting in some SMN2 including exon 7 and some SMN2 lacking exon 7. Cells transfected with ASOs comprising 2'MOE showed increased inclusion of exon 7 in SMN2 compared to untreated control.

Cells transfected with ASOs comprising 2'F showed increased exclusion of exon 7 in SMN2 compared to untreated control—the opposite of the 2'MOE ASOs.

Example 3

Hydridization Dependence of Exon Skipping

To confirm that the observed increase in exon exclusion depended on hybridization of the antisense compound, ISIS 413147 and two mismatched controls each having the same chemistry as ISIS 413147 and having the same nucleobase composition scrambled to include 6 mismatched positions were prepared. The sequences are provided in the table below.

| ISIS No. | Sequence | TSS ID | SEQ ID NO |
|---|---|---|---|
| 447438 | $T_eT_eA_fG_fU_fU_fU_fA_fA_fU_fC_fA_fC_fG_fC_fU_f{}^{Me}C_eG_e$ | I061216 | 5 |
| 447439 | $T_e{}^{Me}C_eA_fU_fU_fU_fG_fC_fU_fU_fC_fA_fU_fA_fC_fA_fG_eG_e$ | I061216 | 6 |
| 413147 | $T_e{}^{Me}C_eA_fC_fU_fU_fU_fC_fA_fU_fA_fA_fU_fG_fC_fU_fG_eG_e$ | I061216 | 7 |

Subscript "e" indicates that the preceding nucleoside comprises a 2'-MOE sugar moiety.
Subscript "f" indicates that the preceding nucleoside comprises a 2'-F sugar moiety.
Superscript "Me" indicates a 5-methyl group on the pyrimidine base of the preceding nucleoside.
All ASOs in the above table had phosphorothioate linkages (PS) throughout.

SMA type I patient fibrorblasts (GM03814, Coriell) were transfected with increasing concentrations of one of the above ASOs or no ASO (control) using Cytofectin under standard conditions. After 24 hours, RNA was isolated and analyzed by RT-qPCR.

Results show that the 2-'F containing ASO induced skipping and the mismatched controls had no effect on splicing.

Example 4

Additional SMN2 Target Cites

ASOs to other target cites of intron 7 of SMN2 were designed as summarized in the table below.

| ISIS No. | Sequence | TSS ID | SEQ ID NO |
|---|---|---|---|
| 461787 | ${}^{Me}C_eT_eT_eT_e{}^{Me}C_eA_eT_eA_eA_eT_eG_e{}^{Me}C_eT_eG_eG_e{}^{Me}C_eA_eG_e$ | I061216 | 8 |
| 467386 | $T_eT_e{}^{Me}C_eA_e{}^{Me}C_eT_eT_eT_e{}^{Me}C_eA_eT_eA_eA_eT_eG_e{}^{Me}C_eT_eG_e$ | I061216 | 9 |
| 467387 | $G_eA_eT_eT_e{}^{Me}C_eA_e{}^{Me}C_eT_eT_eT_e{}^{Me}C_eA_eT_eA_eA_eT_eG_e{}^{Me}C_e$ | I061216 | 10 |
| 467388 | $A_eA_eA_eG_eT_eA_eA_eG_eA_eT_eT_e{}^{Me}C_eA_e{}^{Me}C_eT_eT_eT_e{}^{Me}C_e$ | I061216 | 11 |
| 467389 | ${}^{Me}C_eT_eU_fU_fC_fA_fU_fA_fA_fU_fG_fC_fU_fG_fG_fC_fA_eG_e$ | I061216 | 12 |
| 467391 | $T_eT_eC_fA_fC_fU_fU_fU_fC_fA_fU_fA_fA_fU_fG_fC_fT_eG_e$ | I061216 | 13 |
| 467392 | $G_eA_eU_fU_fC_fA_fC_fU_fU_fU_fC_fA_fU_fA_fA_fU_fG_e{}^{Me}C_e$ | I061216 | 14 |
| 467393 | $A_eA_eA_fG_fU_fA_fA_fG_fA_fU_fU_fC_fA_fC_fU_fU_fT_e{}^{Me}C_e$ | I061216 | 15 |

Subscript "e" indicates that the preceding nucleoside comprises a 2'-MOE sugar moiety.
Subscript "f" indicates that the preceding nucleoside comprises a 2'-F sugar moiety.
Superscript "Me" indicates a 5-methyl group on the pyrimidine base of the preceding nucleoside.
All ASOs in the above table had phosphorothioate linkages (PS) throughout.

The ASOs were tested in SMA type I patient fibroblasts as described in Example 3. Each of the 2'-F containing ASOs resulted in an increase in exon 7 exclusion. ASO's having the same sequence, but having uniform 2'-MOE nucleosides result in increased exon 7 inclusion.

Example 5

ASOs Targeting Pyruvate Kinase Pre-mRNA

The pyruvate kinase M (PK-M) gene has 12 exons, of which exons 9 and 10 are alternatively spliced in a mutually exclusive fashion. Transcripts that include exon 10 encode for an isoform of PK-M that promotes tumorigenesis. We determined if a 2'-F ASO could skip of exon 10 in favor of exon 9. ASOs complementary to nucleotides 11 through 28 downstream of the intron 10 5' splice site of pyruvate kinase were designed as summarized in the table below.

| ISIS No. | Sequence | TSS ID | SEQ ID NO |
|---|---|---|---|
| 466967 | $T_e{}^{Me}C_e{}^{Me}C_eA_eG_eG_eG_eA_eG_e{}^{Me}C_e{}^{Me}C_eG_e{}^{Me}C_eT_eG_e{}^{Me}C_e{}^{Me}C_eG_e$ | I049208 | 16 |
| 466968 | $A_eT_eT_e{}^{Me}C_e{}^{Me}C_eA_eG_eG_eG_eA_eG_e{}^{Me}C_e{}^{Me}C_eG_e{}^{Me}C_eT_eG_e{}^{Me}C_e$ | I049208 | 17 |
| 466969 | $G_eG_e{}^{Me}C_eA_eT_eT_e{}^{Me}C_e{}^{Me}C_eA_eG_eG_eG_eA_eG_e{}^{Me}C_e{}^{Me}C_eG_e{}^{Me}C_e$ | I049208 | 18 |
| 466979 | $T_e{}^{Me}C_eC_fA_fG_fA_fG_fA_fG_fC_fC_fG_fC_eU_fG_fC_f{}^{Me}C_eG_e$ | I049208 | 19 |
| 466980 | $A_eT_eU_fC_fC_fA_fG_fA_fG_fA_fG_fC_fC_fG_fC_fU_fG_e{}^{Me}C_e$ | I049208 | 20 |
| 466981 | $G_eG_eC_fA_fU_fU_fC_fC_fA_fG_fG_fG_fA_fG_fC_fC_fG_e{}^{Me}C_e$ | I049208 | 21 |

Subscript "e" indicates that the preceding nucleoside comprises a 2'-MOE sugar moiety.
Subscript "f" indicates that the preceding nucleoside comprises a 2'-F sugar moiety.
Superscript "Me" indicates a 5-methyl group on the pyrimidine base of the preceding nucleoside.
All ASOs in the above table had phosphorothioate linkages (PS) throughout.

HeLa cells were transfected with 30 nM ASOs as described in Example 1 and were analyzed by RT-PCR and subsequent digestion with Nco I or Pst I as described (see e.g., Clower et al., PNAS 107, 5: 1894-1899, Feb. 2, 2010).

As with SMN2, the 2'-F containing ASOs induced exon skipping and the corresponding 2'MOE ASOs did not. The table below provides the ratio of exon 9 retained to skipped.

| Treatment | Exon9:Exon10 |
|---|---|
| No ASO | 0.06 |
| Uniform MOE | 0.02 |
| MOE-F-MOE (2-14-2) | 0.37 |

Example 6

Assessment of hnRNP Interference by ASOs

To determine if the above observed results could be attributed to the differential recruitment of hnRNP proteins to the target nucleic acid by the 2'-F ASO compared to MOE ASO, ASO/RNA duplexes were captured as follows.

A 23 nucleoside-long portion of SMN2 intron 7 (CUGC-CAGCAUUAUGAAAGUGAAU (SEQ ID NO: 22)) was biotinylated at the 3' end and attached to a streptavidin coated magnetic bead. Samples of that bead-bound intron 7 RNA were incubated with one of (1) 2'-MOE ASO (396443); (2) 2'-MOE/2'-F gapmer ASO (413147); or (3) no ASO (control). The samples were then incubated for 40 minutes at 30° C. with nuclear extracts. Following incubation, the magnetic beads were used to collect the bound intron 7 RNA from the solution and were washed 3 times with 150 mM KCl. Any captured proteins were eluted off the bead bound intron 7 RNA with Laemmli buffer and samples were analyzed by western blot, with antibodies for hnRNP A1 &A2.

The western blots confirmed the presence of the hnRNPs in the untreated control samples. Thus, in the absence of antisense oligonucleotide, hnRNP A1/A2 binds to this target region of intron 7 of SMN2.

The western blot showed that the hnRNPs were absent or reduced in the samples treated either with 2'-MOE ASO or with 2'-F ASO. Thus, both ASOs equally interfere with binding of hnRNPs.

Example 7

Assessment of Protein Recruitment

The differential activity of the 2'-MOE and 2'-F in the splicing assays (Example 2, 4 &5) cannot be explained by the differential recruitment of hnRNPs (Example 6). Thus we explored if the results could be attributed to the differential recruitment of one or more proteins to the target nucleic acid by the 2'-F ASOs. Again ASO/RNA duplexes were captured but this time with a 25 nucleotide long RNA, wherein the 18 nucleotides at the 5'-end were complementary to the ASOs and the 7 3'-most nucleotides (closest to the bead) were randomly selected nucleotides to create a linker. The bead-bound RNA was incubated with ASO and nuclear extracts as in Example 6 to allow formation of complexes comprising cellular proteins and the ASO/bead bound RNA. The magnets were used to isolate the complexes, which were washed 3 times with 300 mM KCl.

After the KCl washes the RNase I was added to the samples to cleave the linker portion of the duplexes and the released complexes were mixed with Laemmli buffer. The samples were run on a gel, which was stained for total protein with Cypro Ruby.

The resulting stained gel showed several bands in the lanes corresponding with 2'F treated samples that were not present in the 2'-MOE treated samples.

Example 8

Identification of Recruited Proteins

Four bands present in the lane corresponding to 2′-F treated samples not present in the 2′-MOE treated samples were excised from the gel and identified by LC-MS.

By LC-MS, the identities of protein were: Interleukin enhancer-binding factor 2 (ILF2), Interleukin enhancer-binding factor 3 (ILF3), RNA Helicase A (RHA), and Nucleophosmin (NPM). The presence of these proteins in the duplexes formed with the 2′-F ASO and not in the duplex with the 2′-MOE ASO was confirmed by Western blot.

Example 9

Knockdown of Recruited Proteins siRNAs directed to each of the four proteins identified in Example 8 (ILF2, ILF3, RHA, and NPM) were purchased (Darmacon). HeLa cells were treated with one of the siRNAs for 2 days, to reduce the amount of each of the proteins.

After 2 days of siRNA treatment, cells were treated for an additional 24 hrs with ISIS 413147 (2-′F ASO complementary to intron 7 of SMN2). RNA was isolated and analyzed by RT-qPCR.

For each of the 4 siRNAs, knockdown was successful, as assessed by RT-qPCR. Knockdown of either ILF2 or ILF3 reversed the 2′-F-ASO-induced exon skipping observed.

Knockdown of either RHA or NPM did not reverse the exon skipping activity of the 2′-F-containing ASO.

Example 10

Other Chemical Modifications

Additional ASOs having different chemical modifications were prepared as described in the table below.

| ISIS No. | Sequence | SEQ ID NO |
|---|---|---|
| 489194 | TCACTTTCATAATGCTGG | 3 |
| 489193 | $U_rC_rA_rC_rU_rU_rC_rA_rU_rA_rA_rU_rG_rC_rU_rG_rG_r$ | 23 |
| 447443 | $T_e{}^{Me}C_eA_rC_rU_rU_rC_rA_rU_rA_rA_rU_rG_rC_rU_rG_eG_e$ | 24 |
| 489191 | $U_fC_fA_fC_fU_fU_fC_fA_fU_fA_fA_fU_fG_fC_fU_fG_fG_f$ | 23 |
| 413147 | $T_e{}^{Me}C_eA_fC_fU_fU_fC_fA_fU_fA_fA_fU_fG_fC_fU_fG_eG_e$ | 24 |
| 493982 | $T_e{}^{Me}C_eA_{fa}{}^{Me}C_{fa}U_{fa}U_{fa}U_{fa}{}^{Me}C_{fa}A_{fa}U_{fa}A_{fa}A_{fa}U_{fa}G_{fa}{}^{Me}C_{fa}U_{fa}G_eG_e$ | 24 |
| 439418 | $U_kC_kA_fC_kU_fU_fU_kC_fA_fU_kA_fA_fU_kG_fC_fU_kG_fG_k$ | 23 |
| 449003 | $U_mC_mA_mC_mU_mU_mU_mC_mA_mU_mA_mA_mU_mG_mC_mU_mG_mG_m$ | 23 |
| 439419 | $U_k{}^{Me}C_eA_eC_kT_eT_eU_k{}^{Me}C_eA_eU_kA_eA_eU_kG_e{}^{Me}C_eU_kG_eG_k$ | 25 |
| 396443 | $T_e{}^{Me}C_eA_e{}^{Me}C_eT_eT_eT_e{}^{Me}C_eA_eT_eA_eA_eT_eG_e{}^{Me}C_eT_eG_eG_e$ | 26 |

Nucleosides not followed by a subscript are β-D-2′-deoxyribonucleosides (DNA). Each nucleoside followed by a subscript "r" is a ribonucleoside (RNA). Nucleosides followed by a subscript indicate modification as follows: subscript "e" indicates the preceding nucleoside comprises a 2′-MOE sugar moiety; subscript "f" indicates the preceding nucleoside comprises a 2′-F sugar moiety; subscript "m" indicates the preceding nucleoside comprises a 2′-OMe sugar moiety. Superscript "Me" indicates a 5-methyl group on the pyrimidine base of the preceding nucleoside. All ASOs in the above table had phosphorothioate linkages (PS) throughout. Nucleosides with subscripts "fa" or "k" are shown below.

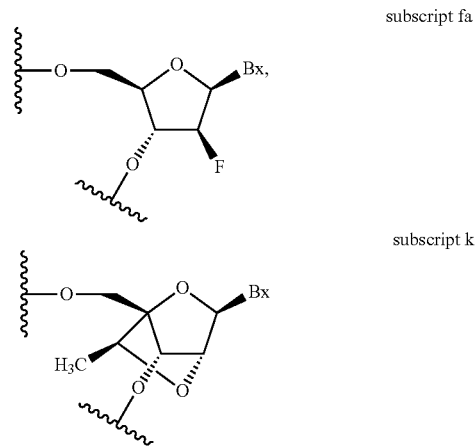

subscript fa subscript k

Figure 2:
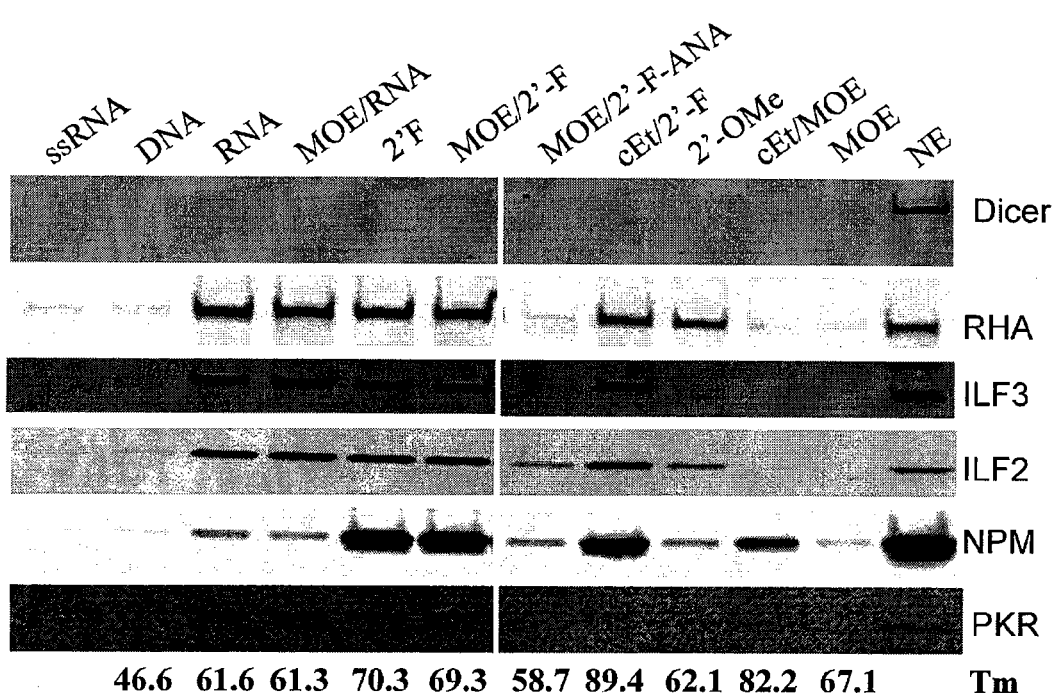
FIG. 2 shows different proteins recruited to duplexes formed by a target RNA and antisense oligonucleotides having different chemical modifications, as described in Example 10.

Each of the above ASOs was tested for its ability to recruit the proteins identified in Example 8. The protocol was similar to that of Example 7, except that rather than RNase I treatment, the samples were treated directly with Laemmli buffer. The samples were run on a gel and a Western blot was performed using antibodies to each of the four proteins identified in Example 8 and antibodies to Dicer, PKR. The blot is reproduced below as FIG. 2.

As is evident from the blot, different chemical modifications of an ASO result in recruitment of different proteins to a duplex formed by the ASO and a target nucleic acid. For example the (S)-cEt/MOE ASO recruits predominantly NPM and the 2′-OMe shows enhanced selectivity for RHA.

Example 11

Interference of U1snRNP

Binding of U1 snRNP at the 5′ splice site of SMN2 intron 7 is important for exon 7 inclusion. It is known that impaired binding of U1 snRNP to a 5′ splice site (i.e., by mutation of the splice site) results in skipping of exon 7. Experiments were performed to determine if the formation of the 2′-MOE/2′-F gapmer ASO/RNA duplex impairs binding of U1 snRNP. This would explain how the 2'-MOE/2'-F gapmer caused exon skipping, while the full MOE ASO caused increase inclusion of SMN2 exon 7. Presumably the full MOE ASO allows more efficient binding of U1 snRNP.

To determine the effects of ASO driven protein binding on U1 snRNP activity, a 34 nucleoside-long portion of SMN2 spanning the exon 6/intron 7 junction (AAGAGUAAGU-CUGCCAGCAUUAUGAAAGUGAAU (SEQ ID NO: 27)) was biotinylated at the 3' end and attached to a streptavidin coated magnetic bead, as described in Example 7. The samples were incubated with one of: (1) ISIS 396443; (2) ISIS 413147; or (3) no ASO (control). The samples were then incubated for 40 minutes at 30° C. with nuclear extracts. Following incubation, the magnetic beads were used to collect the bound RNA from the solution and were washed 3 times with 150 mM KCl. Any captured proteins were eluted off the bead bound RNA with Laemmli buffer and samples were analyzed by western blot, with an anti-U170 antibody, which recognizes a subunit of U1 snRNP.

The Western blot showed that incubation with ISIS 413147 (full MOE) resulted in a strong signal, indicating a high degree of binding of U1snRNP. Incubation with ISIS 413147 (MOE/F gapmer) resulted in greatly reduced U1snRNP. Thus, it appears that ISIS 413147 hybridizes to inton 7, forming a duplex that recruits proteins, such as ILF2 and ILF3, and these in turn prevent binding of U1snRNP, ultimately resulting in skipping of exon 7.

Example 12

Modulation of Splicing of Bcl-X

Bcl-X has two alternative 5' splice sites ($X_S$ upstream and $X_L$ downstream) that compete for a common 3' splice site. Utilization of the $X_S$ or the $X_L$ splice site results in the production of pro-apoptotic or anti-apoptotic Bcl-X protein isoforms, respectively. HeLa cells were transfected with either (1) a uniform 2'MOE modified antisense compound complementary to nucleotides 17 through 34 downstream of the $X_L$ splice site, (2) an antisense compound having the same sequence but having 2-14-2 (MOE/F/MOE) modification motif, or (3) no antisense control. After 24 hours, RNA was collected and analyzed by RT-PCR. Compared to the 2'-MOE ASO, the 2'-F ASO further decreased the use of the $X_L$ splice site and increased the use of the $X_S$ splice site as seen in the table below which provides the ratio of the long form to short form of Bcl-X.

| Treatment | Bcl-$X_L$:Bcl-$X_s$ |
| --- | --- |
| No ASO | 4.2 |
| Uniform 2'-MOE | 1.3 |
| MOE-F-MOE (2-14-2) | 0.7 |

Example 13

Modulation of Splicing in Mice as a Function of ASO Chemistry

Figure 3A:
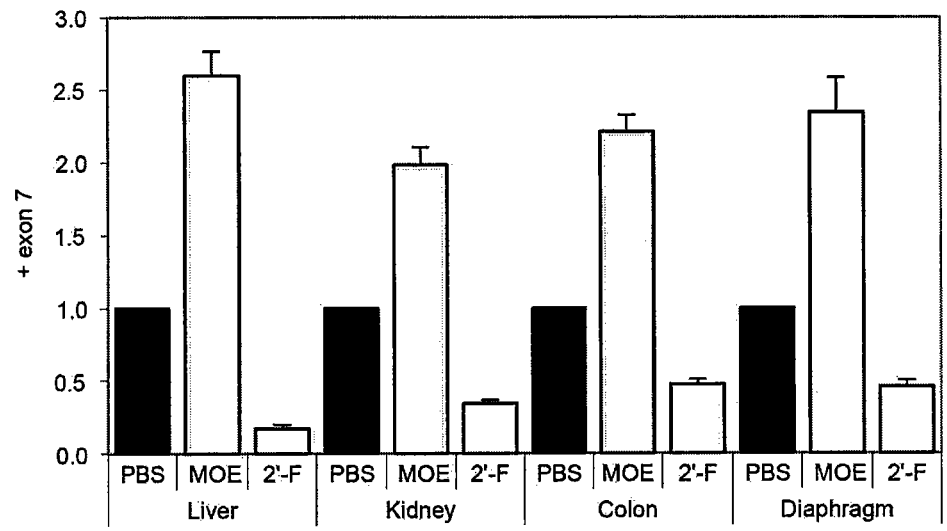
FIGS. 3a and b show the effect of antisense oligonucleotides having different 2'-modified nucleosides on splicing of SMN1 and SMN2 administered to transgenic mice, as described in Example 13. As was the case in cell culture, the uniform MOE-modified antisense compound promoted exon 7 inclusion in each tissue, while the 2'-F compound promoted exon 7 skipping.

Adult SMA type III mice (Smn–/–; SMN2+/+) were obtained from Jackson Laboratory (FVB.Cg-Tg(SMN2) 2HungSMN1tm1Hung/J, stock number 005058). Five mice were treated with ISIS 396443(2'-MOE modified); five mice were treated with ISIS 413147 (2'-F with two 2'-MOE at each end); and five were treated with PBS as control. The ASOs, dissolved in PBS, were administered by intraperitoneal injection at 50 mg/kg/dose every 2 days for a total of 4 doses. The mice were sacrificed 48 hr after the last dose. For extraction of RNA, a 3 mm3 piece of tissue was homogenized in a 2 ml tube containing Lysing Matrid D (MP Biomedicals), 500 µl RLT buffer (Quiagen) and 1% (v/v) β-mercaptoethanol. Homogenization was performed for 20 s at 6,000 rpm using a FastPrep Automated Homogenizer (MP Biomedicals). 10 µl of lysate was used to isolate RNA with the RNeasy 96 Kit (Qiagen) and real-time RT-PCR was performed. Results are shown in FIG. 3.

Figure 3B:
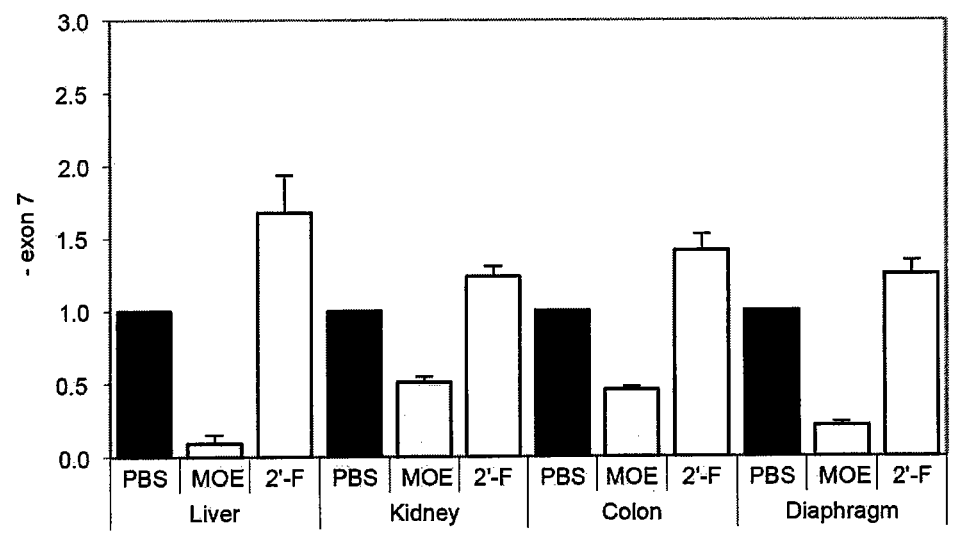

As expected, ISIS 396443 (full 2'-MOE modified) promoted exon 7 inclusion in all tissues examined; this was seen as an increase (relative to control) in transcripts that included exon 7 (FIG. 3a) and a concomitant decrease in transcripts that skipped exon 7 (FIG. 3b). As was the case in cell culture, ISIS 413147 (2'-F with two 2'-MOE at each end) showed the opposite effect on splicing: a decrease in transcripts that included exon 7 (FIG. 3a) and an increase in transcripts that skipped exon 7 (FIG. 3b).

Example 14

Modulation of Splicing Additional Chemical Modification Motifs

Figure 4A:
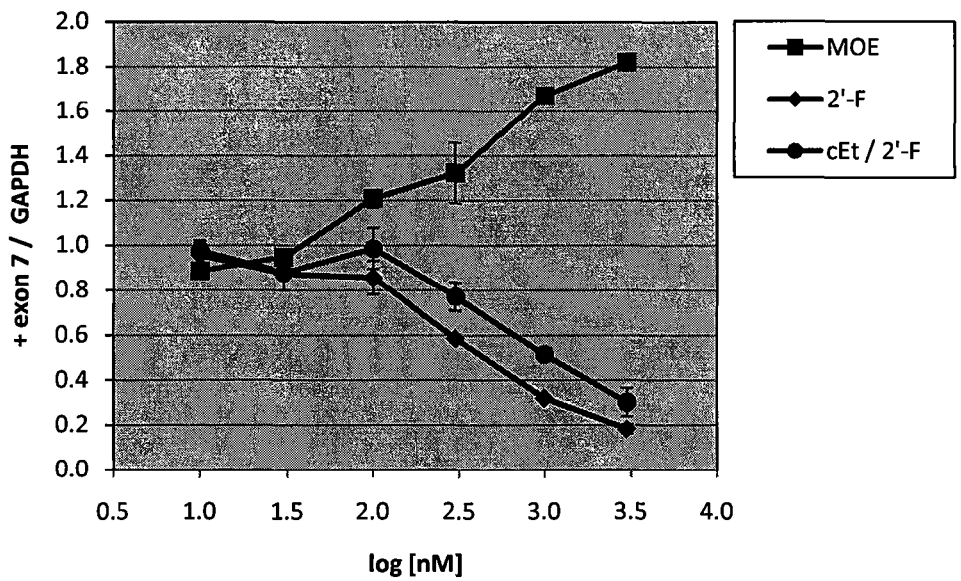
FIGS. 4a and b show the effect of antisense oligonucleotides on splicing of SMN2 in fibroblasts from human SMA type 1 patients, described in Example 14.
Figure 4B:
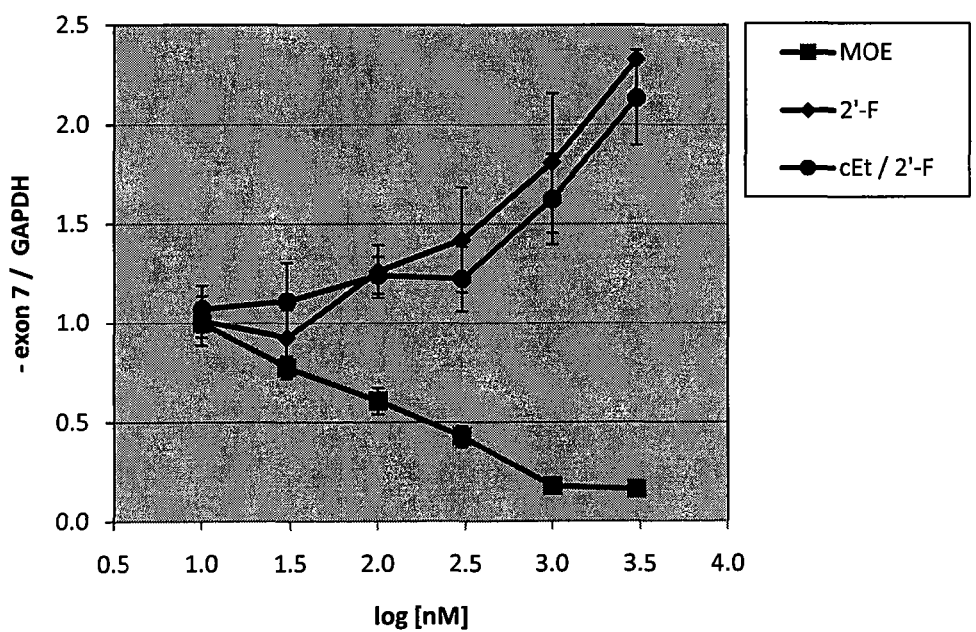

ISIS 396443, ISIS 413147, and ISIS 439418, each of which is shown in the table in Example 10, were tested in SMA type I patient fibrorblasts as described in Example 3. After 24 hours, RNA was isolated and analyzed by RT-qPCR. Results are shown in FIG. 4. The full MOE oligonucleotide (ISIS 396443) resulted in an increase in SMN2 with exon 7 (FIG. 4a) and a decrease in SMN2 lacking exon 7 (FIG. 4b). Both the oligonucleotide having 2'-F with MOE wings (ISIS 413147) and the mixed 2'-F/cEt oligonucleotide had the opposite effect: a decrease in SMN2 with exon 7 retained (FIG. 4a) and an increase in SMN2 lacking exon 7 (FIG. 4b).

The invention claimed is:

1. A method of inducing exon skipping in a target pre-mRNA in a cell comprising contacting the cell with an antisense compound comprising a chemically modified oligonucleotide consisting of 18 linked nucleosides; and thereby inducing exon skipping in the pre-mRNA in the cell; wherein the antisense compound comprises:
   a 5'-wing region consisting of 2 linked duplex stabilizing nucleosides;
   a 3'-wing region consisting of 2 linked duplex stabilizing nucleosides; and
   a central gap region located between the 5'-wing region and the 3'-wing region
   and consisting of 14 contiguous nucleosides comprising 2'-F modifications;
wherein each duplex stabilizing nucleoside is a 2'-methoxyethyl (2'-MOE) nucleoside, and
wherein the antisense compound is complementary to an intron of the target pre-mRNA.

2. The method of claim 1, wherein the antisense compound binds to the target pre-mRNA and recruits at least one non-cleaving nucleic acid binding protein to the antisense compound/target pre-mRNA duplex.

3. The method of claim 2, wherein at least one of the at least one non-cleaving nucleic acid binding proteins recruited to the compound/target pre-mRNA duplex is Interleukin Enhancer Binding Factor 2 or Interleukin Enhancer Binding Factor 3.

4. The method of claim 1, wherein the target pre-mRNA is associated with a disease or disorder.

5. The method of claim 4, wherein the target pre-mRNA is Bcl-x.

6. The method of claim 4, wherein the disease or disorder is cancer.

7. The method of claim 4, wherein the disease or disorder is Duchenne muscular dystrophy.

8. The method of claim 1, wherein the cell is in vitro.

9. The method of claim 1, wherein the cell is in an animal.

10. The method of claim 1 comprising performing an assay to determine whether the exon has been skipped.

11. The method of claim 1 comprising performing an assay to determine whether a protein has been recruited to the antisense compound/target pre-mRNA duplex.

12. The method of claim 11 comprising performing an assay to determine the identity of one or more protein recruited to the antisense compound/target pre-mRNA duplex.

13. The method of claim 6, wherein the cell is in an animal.

14. The method of claim 7, wherein the cell is in an animal.

* * * * *

UNITED STATES PATENT AND TRADEMARK OFFICE
CERTIFICATE OF CORRECTION

| | | |
|---|---|---|
| PATENT NO. | : 9,518,259 B2 | Page 1 of 1 |
| APPLICATION NO. | : 13/703322 | |
| DATED | : December 13, 2016 | |
| INVENTOR(S) | : Frank Rigo et al. | |

It is certified that error appears in the above-identified patent and that said Letters Patent is hereby corrected as shown below:

In the Specification

Column 1, Line 14 insert the following:

--This invention was made with government support under GM042699 awarded by The National Institutes of Health. The government has certain rights in the invention.--

Signed and Sealed this
Thirteenth Day of June, 2017

Joseph Matal
*Performing the Functions and Duties of the*
*Under Secretary of Commerce for Intellectual Property and*
*Director of the United States Patent and Trademark Office*